United States Patent
Singer et al.

(10) Patent No.: US 10,130,658 B2
(45) Date of Patent: Nov. 20, 2018

(54) METHOD OF EX VIVO ENHANCEMENT OF IMMUNE CELL ACTIVITY FOR CANCER IMMUNOTHERAPY WITH A SMALL MOLECULE ABLATIVE COMPOUND

(71) Applicants: Jamie Singer, Knoxville, TN (US); Eric Wachter, Oak Ridge, TN (US); Amod Sarnaik, Tampa, FL (US); Shari Pilon-Thomas, Tampa, FL (US); Hao Liu, Tampa, FL (US)

(72) Inventors: Jamie Singer, Knoxville, TN (US); Eric Wachter, Oak Ridge, TN (US); Amod Sarnaik, Tampa, FL (US); Shari Pilon-Thomas, Tampa, FL (US); Hao Liu, Tampa, FL (US)

(73) Assignees: Provectus Pharmatech, Inc., Knoxville, TN (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 14/974,357

(22) Filed: Dec. 18, 2015

(65) Prior Publication Data
US 2017/0173079 A1 Jun. 22, 2017

(51) Int. Cl.
| | |
|---|---|
| A61K 35/15 | (2015.01) |
| A61K 35/17 | (2015.01) |
| A61K 38/17 | (2006.01) |
| A61K 38/21 | (2006.01) |
| A61K 39/00 | (2006.01) |
| C07K 16/28 | (2006.01) |
| C12P 21/00 | (2006.01) |
| A61K 31/352 | (2006.01) |
| C12P 21/02 | (2006.01) |
| A61K 39/395 | (2006.01) |

(52) U.S. Cl.
CPC ............ *A61K 35/17* (2013.01); *A61K 31/352* (2013.01); *A61K 35/15* (2013.01); *A61K 38/1709* (2013.01); *A61K 38/217* (2013.01); *A61K 39/0011* (2013.01); *A61K 39/3955* (2013.01); *C07K 16/2803* (2013.01); *C12P 21/005* (2013.01); *C12P 21/02* (2013.01); *A61K 2039/5154* (2013.01); *A61K 2039/5158* (2013.01); *C07K 2317/76* (2013.01)

(58) Field of Classification Search
None
See application file for complete search history.

(56) References Cited

U.S. PATENT DOCUMENTS

2011/0123483 A1 5/2011 Roth et al.

FOREIGN PATENT DOCUMENTS

| WO | WO2012/122444 | * | 9/2012 |
| WO | WO 2012/170742 A2 | | 12/2012 |

OTHER PUBLICATIONS

Becker et al (Nature Medicine, 2001, vol. 7, pp. 1159-1162).*
Toomey, P. et al, "Intralesional Injection of Rose Bengal Induces a Systemic Tumor-Specific Immune Response in Murine Models of Melanoma and Breast Cancer," PLOS ONE, vo. 8, No. 7, Jul. 2013, pp. 1-6.
Meijer, S. L. et al., "Adoptive Cellular Therapy with Tumor Vaccine Draining Lymph Node Lymphocytes After Vaccination with HLA-B7/$\beta_2$—Microglobulin Gene-Modified Autologous Tumor Cells," Journal of Immunotherapy, vol. 25, No. 4, Jul. 1, 2002, pp. 359-372.
Chang, A.E. et al, "Current Status of Adoptive Immunotherapy of Cancer," Critical Reviews in Oncology/Hematology, vol. 22, No. 3, Jan. 1, 1996, pp. 213-228.
Liu, H. et al, "Intralesional Rose Bengal in Melanoma Elicits Tumor Immunity via HMGB1," Journal for Immunotherapy of Cancer, vol. 3, No. 2, Nov. 4, 2015, p. 1.
Li, Q. et al, "Adoptive Transfer of Tumor Reactive B Cells Confers Host T-Cell Immunity and Tumor Regression," Clinical Cancer Research, vol. 617, No. 15, Jun. 20, 2011, pp. 4987-4995.
Pilon-Thomas, S. et al, "Blockade of Programmed Death Ligand 1 Enhances the Therapeutic Efficacy of Combination Immunotherapy Against Melanoma," Journal of Immunology, vol. 184, No. 7, Apr. 1, 2010, pp. 3442-3449.
Wachter, E.A. et al, "Abstract 4755: Combination of PV-10 Immuno-chemoablation and Systemic Anti-CTLA-4 Antibody Therapy in Murine Models of Melanoma," Proceedings: 104th Annual Meeting of American Association for Cancer Research, Washington DC, Apr. 6-10, 2013, Cancer Research, vol. 73, No. 8, suppl., Apr. 6, 2013, (4 pages).
International Search Report re Application No. PCT/US2016/065542, dated Mar. 28, 2017.
Written Opinion re Application No. PCT/US2016/065542, dated Mar. 28, 2017.
Thompson et al., *Ann Surg Oncol.* 22:2135-2142 (2015).
Hinrichs et al., *Immunol Rev* (Jan. 2014) 257(1):56-71.
Goff et al., *J Immunother* (2010) 33:840-847.
Pilon-Thomas et al., *J Immunother* (Oct. 2012) 35(8):615-620.
Kodumudi et al., (Oct. 2012) *J Immunol* 189:5147-5154.
Radvanyi et al., *Clin Cancer Res* (2012) 18(24):6758-6770.
Dr. Eric Wachter *Curriculum Vitae.*

* cited by examiner

*Primary Examiner* — Karen A. Canella
(74) *Attorney, Agent, or Firm* — Husch Blackwell LLP

(57) ABSTRACT

A cancer immunotherapy method is disclosed in which "induced immune anticancer agents" are isolated after being induced in an animal host by intralesional (IL) administration of a halogenated xanthene tumor-ablative compound into a solid cancerous tumor of that host animal. A sample of the induced immune anticancer agents is removed (collected) from the tumor-bearing host, banked if desired, cultured and preferentially expanded to form an immunologically-effective enriched tumor-specific immune anticancer agent composition. That composition is reintroduced in to the host from which the predecessor induced immune anticancer agents were taken, or into another immunologically suitable host in need.

26 Claims, 25 Drawing Sheets

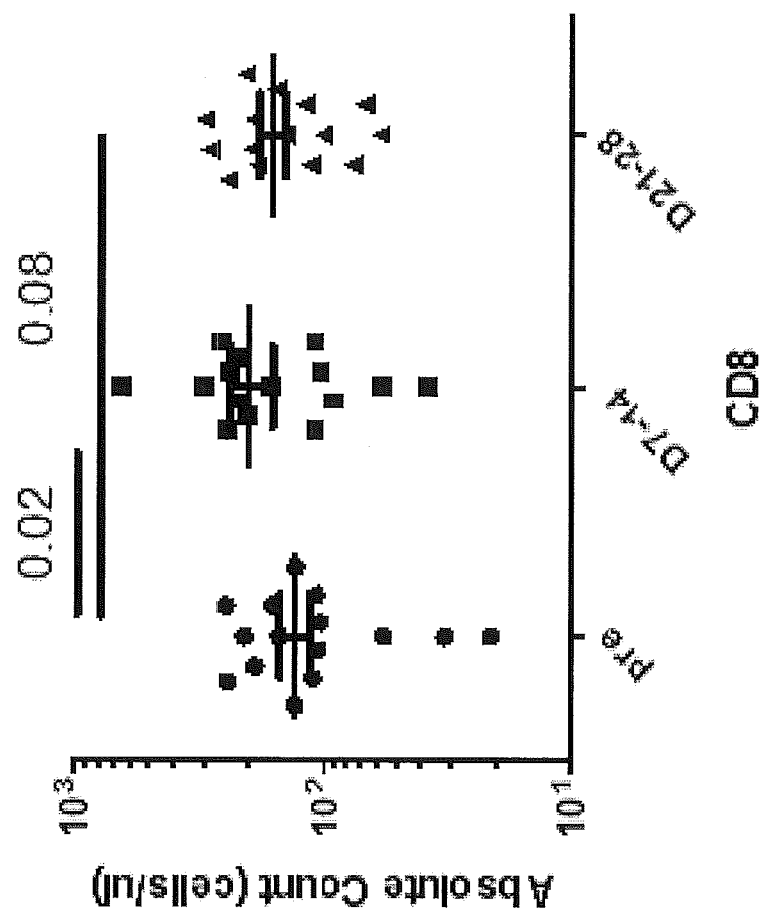

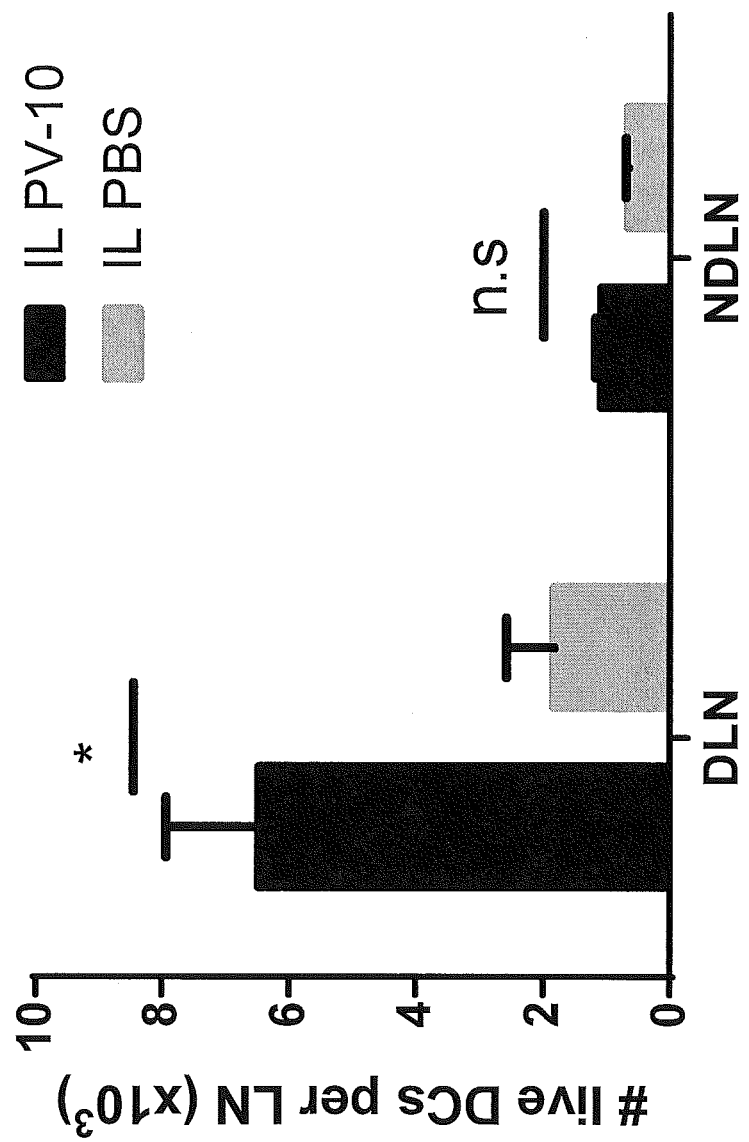

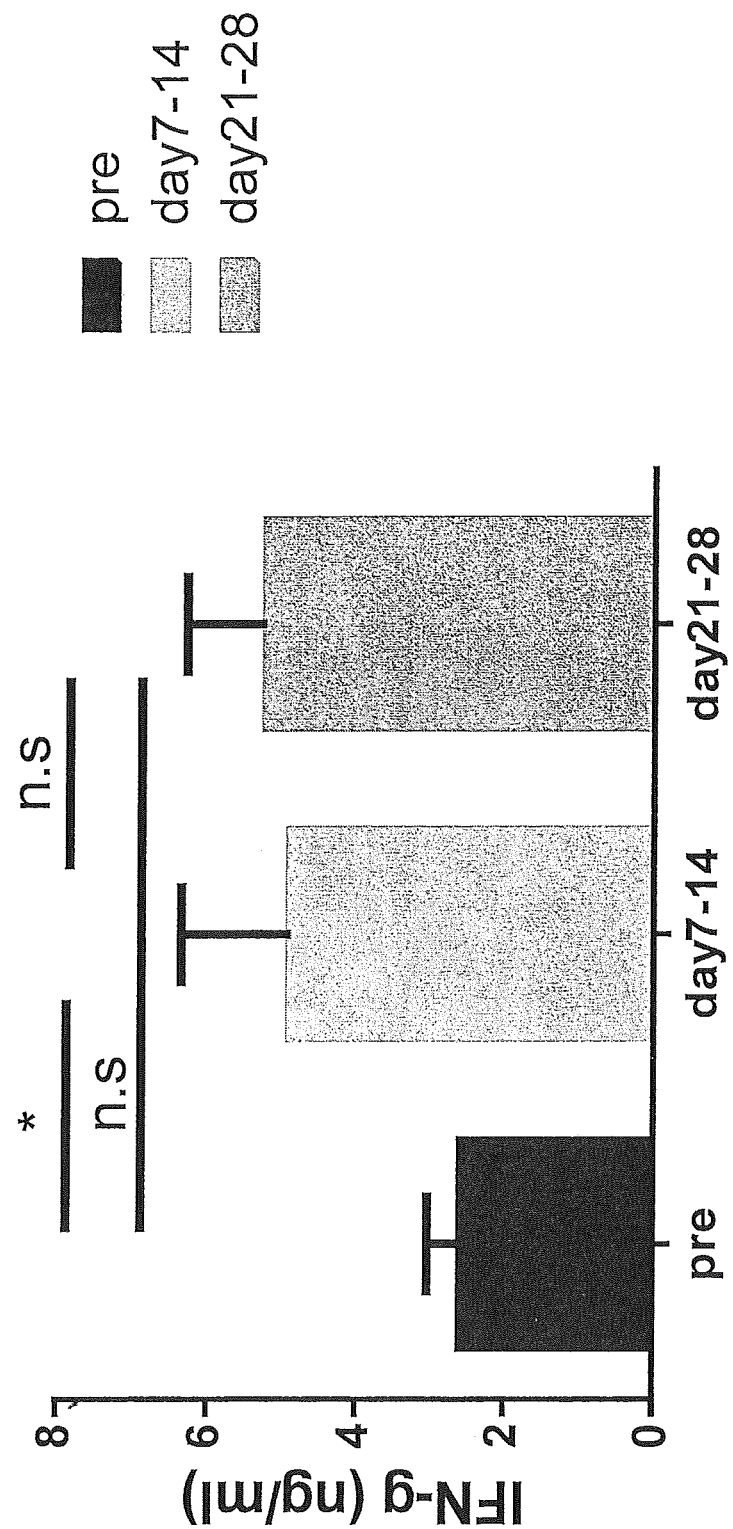

METHOD OF EX VIVO ENHANCEMENT OF IMMUNE CELL ACTIVITY FOR CANCER IMMUNOTHERAPY WITH A SMALL MOLECULE ABLATIVE COMPOUND

TECHNICAL FIELD

The present invention relates to a method of enhancing immune cell activity with intralesional injection of a small molecule halogenated xanthene tumor-ablative compound to induce immune system components within the peripheral blood, tumor tissue or lymphoid tissue of a mammal. Members of the induced immune system components are collected, expanded ex vivo and then reintroduced into the mammal from which they originated as an enriched tumor-specific immune anticancer agent composition.

BACKGROUND OF THE INVENTION

Immunotherapeutic strategies incorporating intralesional (IL) therapy to elicit tumor specific immune responses can serve as a non-surgical option for cutaneous neoplasms. These strategies haven been shown to induce both local and systemic tumor regressions. Intratumoral injection of dendritic cells (DCs), IL-2, and GM-CSF and treatment with adjuvant Bacille Calmette-Guérin (BCG) or toll-like receptor (TLR) agonists have been shown to enhance systemic anti-tumor immunity in both melanoma tumor-bearing mice and in patients with advanced melanoma [Triozzi et al., Cancer 89:2646-2654 (2000); Pilon-Thomas et al., J Immunother 29:381-387 (2006); Guo et al., Int J Cancer 120: 2418-2425 (2007); Kaufman et al., Ann Surg Oncol 17:718-730 (2010); Kidner et al., J Immunother 35:716-720 (2012)]. Dendritic cells are the most potent antigen presenting cells (APCs) and can prime an immune response by T cells that have not been exposed to the antigen previously [Small et al., J Clin Oncol 18:3894-3903 (2000)].

In the $20^{th}$ century, several uses for fluorescein analogs emerged. The compounds have been used as textile dyes, biological stains, building blocks for non-volatile memory devices, thermoimaging substrates and food and cosmetics coloring. For example, erythrosine (FD&C No. 3) and partially iodinated erythrosine (D&C Nos. 11 and 12) are used as food, drug and cosmetic dyes. A particular tetraiodo xanthene, rose bengal, has been used for visualization of ocular disease and, in radiolabeled form, as a medical diagnostic for liver function, appearing in the United States Pharmacopeia in 1965.

Use of rose bengal (RB) as a biological stain by ophthalmologists and in liver function studies became common in the $20^{th}$ century [Norn, Acta Ophthalmol 48:546-559 (1970); Delprat Arch. Int. Med. 32:401-410 (1923)]. RB can kill both microorganisms and cancer cells as a photodynamic sensitizer or even without laser activation for metastatic melanoma and ovarian cancer [Banks et al., J Appl Bact 58:391-400 (1985); Koevary, Int J Physiol Pathophysiol Pharmacol 4:99-107 (2012); Thompson et al., Melanoma Res 18:405-411 (2008); Wachter et al., Proc. SPIE 4620: 143-147 (2002)].

RB can pass through the cell membrane and accumulate in the lysosomes of tumor cells and autolyse tumor cells within 30-60 minutes, while it is excluded from normal cells [Wachter et al., Proc. SPIE 4620:143-147 (2002)]. Notably, IL therapy of PV-10 (10% rose bengal in PBS; Provectus Biopharmaceuticals, Inc., Knoxville, Tenn.) has been shown to elicit tumor-specific immunity in human studies [Thompson et al., Melanoma Res 18:405-411 (2008); and Thompson et al., Ann Surg Oncology 22:2135-2142 (2015)] manifested in un-injected bystander lesion regression. Further studies revealed that IL PV-10 treatment can induce T-cell mediated tumor-specific immune responses in MT901 breast cancer and in B16 melanoma mouse models [Toomey et al., PloS one 8:e68561 (2013)]. However, the underlying mechanisms remain unknown.

Thus, rose bengal has been disclosed as an ablative agent patented for tumor destruction (U.S. Pat. No. 8,557,298). A novel action of post rose bengal ablation is the ability of immune system components to recognize tumor tissue in situ in the treated mammal. These immune system components have been found to induce a systemic immune system response in the ablation-treated mammal.

A number of strategies have been proposed to induce immune responses as a treatment strategy in cancer. These approaches generally consist of removing diseased tissue from the host and manipulating that tissue to target, treat or expand in size or number, useful immune system components prior to readministration of the immune components to the host.

For example, vaccines comprised of dendritic cells pulsed ex vivo with tumor antigens and expansion of natural killer cells are under investigation (U.S. Pat. No. 8,597,946). Antigen- and non-antigen-based antibodies have been manufactured and manipulated ex vivo to target tumor tissue (U.S. Pat. No. 8,153,120, US 2004/0161413 A1). Notably, a combination of non-myeloablative chemotherapy and adoptive transfer of expanded T-cells has been reported to result in sustained clinical responses in late-stage cancer patients [Pilon-Thomas, J. Immunother 35(8):615-620 (2012)]. These strategies are independent of endogenous immune tissue and are manufactured ex vivo from extracted tumor tissue or peripheral blood for administration to patients. Additionally, the use of non-myeloablative chemotherapy adds additional time and cost to the treatment, and can enhance the possibility of increased treatment-based morbidity.

Dying cancer cells can release soluble molecules known as damage-associated molecular pattern molecules (DAMPs), which are mainly recognized by pattern recognition receptors (PRRs) [Zitvogel et al., Cell 140:798-804 (2010)]. Particular DAMPs can serve as powerful immunological adjuvants for cancer therapy [Kroemer et al., Ann Rev Immunol 31:51-72 (2013); Krysko et al., Nature Rev Cancer 12:860-875 (2012)]. These DAMPs include several members of the heat shock protein (HSP) family, the S100 proteins, ATP, IL-1α and high mobility group box 1 (HMGB1), also known as amphoterin [reviewed by Panzarini et al., PloS one 9:e105778 (2013)].

HMGB1 is an abundant protein bound to DNA in almost all eukaryotic cells. Its putative receptors include the receptor for advanced glycation end-products (RAGE), Toll-like Receptor-2 (TLR2), TLR4 and T cell immunoglobulin-3, (TIM-3) (Taguchi et al., Nature 405:354-360 (2000); Park et al., J Biol Chem 279:7370-7377 (2004); Chiba et al., Nature Immunol 13:832-842 (2012)]. HMGB1 has a membrane-bound form and also can be secreted into the extracellular space as a cytokine-like factor. It is secreted from activated immune cells such as macrophages and dendritic cells (DCs) after its acetylation, or can be released by necrotic, apoptotic and autophagic cancer cells as a DAMP [Scaffidi et al., Nature 418:191-195 (2002); Bonaldi et al., EMBO J 22:5551-5560 (2003); Kazama et al., Immunity 29:21-32 (2008); Thorburn et al., Cell Death Differ 16:175-183. (2009)].

HMGB1 plays an important role in the activation of endothelial cells, promotion of angiogenesis, immune cell migration, and initiation of inflammation [Lotze et al., Nature Rev Immunol 5:331-342 (2005)]. Although HMGB1 has been shown to contribute to tumor metastasis and neoangiogenesis, its release by dying tumor cells can lead to the activation of DCs to prevent tumor progression [Apetoh et al., Nature Med 13:1050-1059 (2007); Curtin et al., PLoS Med 6:e10 (2009)].

There are many ways known to isolate, bank, expand, target, and retreat cancer patients with tissues designed to stimulate immune system anti-tumor activity. Some strategies such as PROVENGE® (SIPULEUCEL-T) and adoptive transfer start with patient peripheral blood, lymphoid or tumor tissue. However, none of these strategies uses an intralesional ablation of tumor tissue to enhance the quality of endogenous immune components in situ prior to their removal from the patient. The post removal treatment strategies can be patient-specific for personalized therapies.

Immunoglobulins (antibodies) and sometimes vaccines to common diseases have been used to enhance an immune response for tumor treatment in a wider patient population. Such antibodies and vaccines are more generalizable to patients from whom they are not necessarily isolated. For example, antibody design using endogenous ligands is generally applicable to a wide variety of patients and these ligands are often discovered after probing a system with a stimulus to elucidate an antibody that is more generalizable.

Similarly, antibodies can be engineered to mimic naturally occurring events in endogenous immune responses to cancer. For example, the anti-CTLA-4 (cytotoxic T lymphocyte-associated antigen 4) monoclonal antibodies ipilimumab and tremelimumab are designed to counter down-regulation of the immune system by blocking CTLA-4 activity and thus augment T-cell response against cancer. Similarly, monoclonal antibodies such as pidilizumab, nivolumab, lambrolizumab and pembrolizumab bind to PD-1 (programmed death 1) receptor to counter down-regulation of the immune system and augment T-cell responses to cancerous tumors. Initial work with antibodies to the PD-1 ligands, PD-L1 and PD-L2, such as BMS-936559, MEDI4736 and atezolizumab (MPDL3280A) to PD-L1, also indicate inhibition of down-regulation of the immune system and an augmented T-cell response against cancer.

Alternative approaches utilize substances that stimulate certain components of the immune system (i.e., up-regulation or down-regulation), including administering non-specific cytokines (such as interleukin-1, -2, or -12; "IL-1", IL-2", or "IL-12"; interferon-alpha or gamma, "IFN-α" and "IFN-γ"; granulocyte macrophage colony stimulating factor, "GM-CSF"), or that attempt to provoke a tumor-specific immune response.

As disclosed hereinafter, it is believed that removal of tissue containing immune cells from a host or tumor cells treated with a halogenated xanthene, such as rose bengal in PV-10, can be used to make general antibodies or personalized therapies. These components could be isolated after exposure to the ablative compound.

Intralesional administration of tumor tissue with a halogenated xanthene (such as that of PV-10) releases tumor antigens that stimulate tumor-specific immune cells found in peripheral blood, local lymphoid tissue or tumor tissue after ablation but not in significant levels in these tissues of a placebo-treated subject. The local antigen-presenting cells are thereby pre-loaded with tumor debris and can be valuable in the treatment of disease on their own merit.

The disclosure that follows shows that IL PV-10 injection can elicit tumor-specific immune responses in illustrative patients with melanoma and in melanoma-bearing mice. It is further found that an underlying mechanism is that IL injection of PV-10 into melanoma tumors leads to the release of HMGB1 and activation of immune cells for the induction of tumor-specific immunity. The induced tumor responses in vivo and in vitro cascade in tumor and immune system tissues whose activated cells can be banked and reintroduced, or expanded and then reintroduced using techniques known in the art to treat or inhibit further episodes of the cancer.

Additionally these locally used ablative agents can be used in mammalian or in vitro studies as a tool to identify an antibody specific to the ablated cells, or as a tool for identification prior to cloning of useful biologic material for the treatment of the cancer. These antibodies can be useful as a more general treatment of cancer either alone or after cloning and manufacturing according to techniques known in the art. The immune components so generated and isolated from peripheral blood, spleen, tumor, or lymph nodes are capable of responding to tumor both in mice and in people and can be detected within about 1 day or more following intralesional injection.

SUMMARY OF THE INVENTION

The present invention contemplates a method of immunotherapy using an "enriched tumor-specific immune anticancer agent composition" derived from "induced immune anticancer components" such as one or more types of immune cells, immunoglobulins, proteins such as antigens, cytokines and other immune components that are isolated after being induced in an animal host by intralesional (IL) administration of a halogenated xanthene tumor-ablative compound such as rose bengal disodium into a solid cancerous tumor of that host animal. A sample of the induced immune anticancer components created by halogenated xanthene tumor ablation is removed (collected) from the tumor-bearing host, banked if desired, or cultured and preferentially expanded to form an enriched tumor-specific immune anticancer agent composition. The enriched tumor-specific immune anticancer agent composition can also be banked if desired, or adjusted to form an immunologically-effective enriched tumor-specific immune anticancer agent composition and reintroduced in to the host from which the predecessor induced immune anticancer components were taken (autologous transfer), or into another immunologically suitable host in need (allogeneic transfer).

Those induced immune anticancer components are collected by removing a sample of one or more of an aliquot of peripheral blood, tumor tissue or lymphoid (lymphocyte-containing) tissue, such as draining lymph nodes, thymus cells and splenic cells. The induced immune anticancer agents are preferably collected about 1 to about 365 days, preferably about 4 to about 90 days and most preferably about 7 to about 14 days, after IL ablation or after repeated ablations. The induced immune anticancer components can be banked by well-known blood banking techniques such as but not limited to freezing, chilling to about 1.0 to about 8.0 C or lyophilization prior to further action being taken.

The induced immune anticancer components present in the sample of peripheral blood, tumor tissue and/or lymphoid tissue are cultured in vitro by known methods of cell culture to form an enriched tumor-specific immune anticancer agent composition. The enriched tumor-specific immune anticancer agent composition can itself be frozen, lyophilized or otherwise stored for later use (banked) as discussed above.

In a preferred embodiment, the tumor-specific immune anticancer agent composition is adjusted to form an immunologically-effective enriched tumor-specific immune anticancer agent preparation that contains an immunologically-effective concentration of enriched tumor-specific immune anticancer agent dissolved or dispersed in a pharmaceutically acceptable diluent, which preparation also has a parenteral injection-appropriate salt content, osmolality and pH value. That preparation is parenterally reintroduced into the host animal from which the induced immune anticancer components were originally taken (autologous administration) or administered to another immunologically appropriate animal (allogeneic administration), or further cultured to provide further immune anticancer agents.

In a further embodiment, the induced immune anticancer components are obtained and administered to a tumor at a location different from the location of the previously described, ablated tumor. This administration can be carried out intralesionally, or by other well-known means of parenteral administration such as by intravenous, subcutaneous or intraperitoneal administration.

This administration is carried out without expansion of the induced immune anticancer components into a tumor-specific immune anticancer agent composition. The induced immune anticancer components can be banked prior to their reintroduction into the host animal.

In another embodiment, this method employs intralesional injection of a halogenated xanthene such as the illustrative rose bengal into tumor tissue to induce interferon-positive T-cells targeted to endogenous tumor tissue. In a further embodiment, this method employs the same ablative exposure of tumor tissue to rose bengal to induce dendritic cells, expose tumor antigens, induce antibodies and patient-specific or patient-independent cellular therapeutics and cytokines.

The present invention has several benefits and advantages.

One benefit of the invention is the provision of an enriched tumor-specific immune anticancer agent composition that can be used as a source of such agents for subsequent use.

An advantage of the invention is that it provides an augmented immunologically-based treatment method for administration to various solid cancerous tumors.

Still further benefits and advantages of the invention will be apparent to those skilled in the art from the disclosure that follows.

BRIEF DESCRIPTION OF THE DRAWINGS

In the drawings, forming a portion of this disclosure,

FIGS. 1D, 1E and 1F illustrate the increased $CD8^+$ T (FIG. 1D), $CD4^+$ T (FIG. 1E), and NKT (FIG. 1F) cells in peripheral blood mononuclear cells (PBMCs) of human patients after treatment (n=14). Numbers in each figure indicated p value along the centered bar. p values were determined by Wilcoxon match-pairs signed rank test. *, $p<0.05$ statistically significant versus pre-treatment; , $p<0.01$; *, $p<0.001$; n.s., not significant.

FIG. 4A is a graph showing the number of dendritic cells (DCs; $CD11c^+$ MHC $II^+$) from tumor draining LNs (DLN) or non-draining LNs (NDLN) from C57BL/6 mice into which $3\times10^5$ M05 cells were injected followed by IL injection of 50 µl PV-10 or PBS on day 7 as measured by flow cytometry 18 hours after IL injection.

FIG. 7 is a graph showing HMGB1 levels present in serum of melanoma patients at days 7-14 and 21-28 post intralesional PV-10 (10% aqueous rose bengal; Provectus Biopharmaceuticals, Inc., Knoxville, Tenn.) treatment therapy relative to the serum amount present prior to treatment. Data are shown as mean±SEM (n=14). *, p<0.05; n.s., not significant. P values were determined by a Wilcoxon matched-pairs signed rank test.

DETAILED DESCRIPTION OF THE INVENTION

Figure 1A:
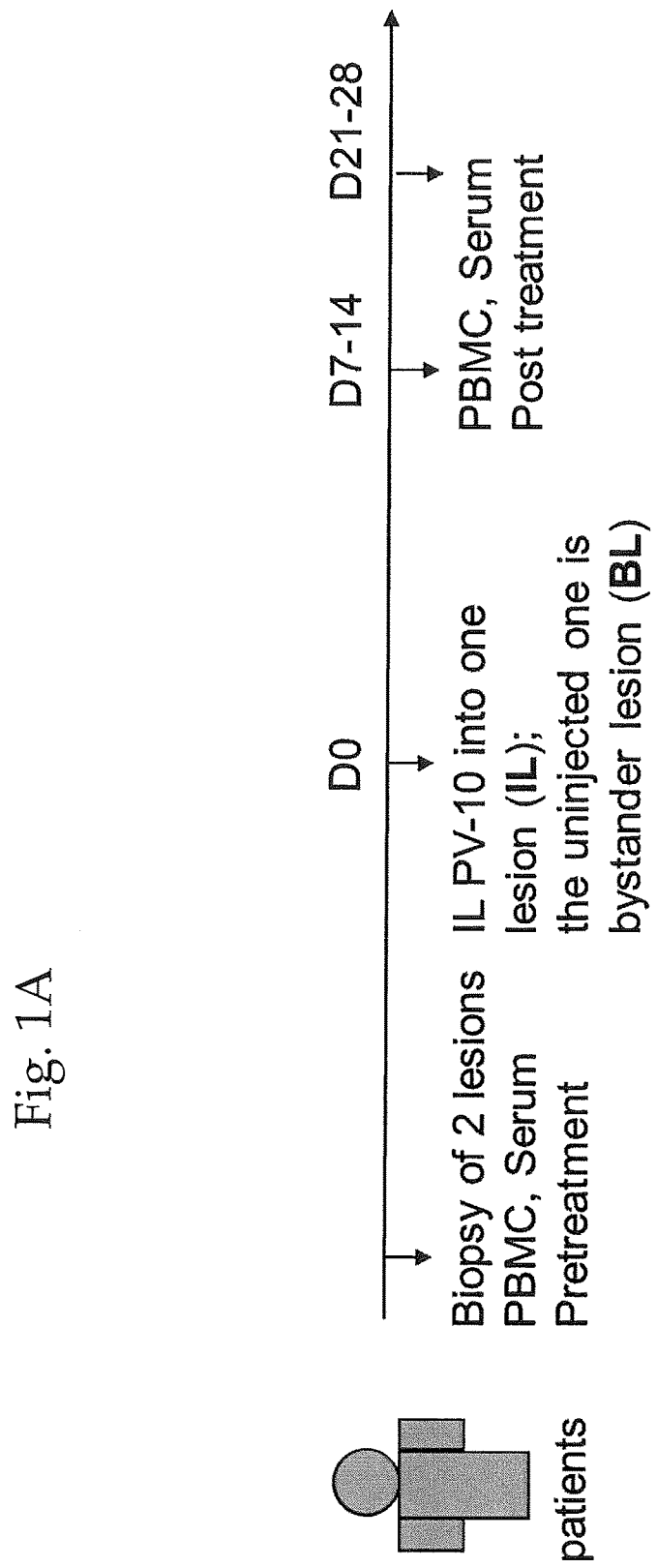
FIG. 1A is a schematic that illustrates clinical study design.

The present invention contemplates a method of forming and using a preparation of enriched tumor-specific immune anticancer components that can later be used immunotherapeutically. The method comprises the steps of (A) contacting tumor tissue in a host animal with a chemoablating pharmaceutical composition comprising a tumor-ablating amount of a halogenated xanthene compound that is preferably dissolved or dispersed in a pharmaceutical composition. Specifics of a chemoablating pharmaceutical composition are discussed separately hereinafter. (B) The host animal is maintained for a time period sufficient (about 1 to about 30 days) for its immune system to produce tumor-specific immune anticancer agents to that tumor; i.e., for induction of tumor-specific immune anticancer agents. (C) A sample comprising one or more of an aliquot of peripheral blood, tumor tissue or lymphoid tissue that contain tumor-specific immune anticancer components is collected (removed) from the animal host. (D) Tumor-specific immune anticancer components present in that sample of peripheral blood, tumor tissue and/or lymphoid tissue are cultured and preferentially expanded in vitro to form an enriched tumor-specific immune anticancer agent composition.

Once the pharmaceutical composition containing a tumor-ablating amount of a halogenated xanthene is administered to a solid tumor of the host animal to contact the cancer cells, the host animal is maintained for at least a period of time sufficient to induce the host animal's immune system to produce tumor-specific immune anticancer agents to said tumor. Typical maintenance times are about 1 to about 30 days post ablating administration of the pharmaceutical composition.

Maintenance in this circumstance is simply permitting the animal to live its normal life, with medical/veterinary observation and/or intervention as is usual and needed following such treatments. For example, phase 2 human clinical trials of 80 patients with Stage IIIB-IV melanoma using an aqueous composition of 10% rose bengal formulated for intralesional injection (PV-10; Provectus Biopharmaceuticals, Inc., Knoxville, Tenn.) injected into tumors found the treatment to be well tolerated, with adverse events confined mainly to the injection site, and no grade 4 or 5 adverse events associated with use of PV-10.

Once the maintenance period is over, a body sample comprising one or more of (1) an aliquot of peripheral blood, (2) tumor tissue and (3) lymphoid tissue that contains tumor-specific immune anticancer components is collected (removed) from the animal host. That sample can be banked (stored) as discussed hereinafter prior to being cultured and preferentially expanded. Alternatively, the tumor-specific immune anticancer components can be introduced into another tumor of the same host animal, after appropriately sizing the solid components and dispersion of those components in an appropriate vehicle for parenteral administration. As noted previously, such parenteral administration can be carried out by intralesional, intravenous, subcutaneous or intraperitoneal or similar administration. Appropriate vehicles for such a dispersion are discussed hereinafter.

Preferred tumor-specific immune anticancer components are of two general types.

A first type of tumor-specific immune anticancer component is an immune cell such as a T cell, B cell, antigen-presenting cell (APC) such as a dendritic cell, NK cell, or monocyte (macrophage). Such cells recognize tumor cell antigens or ablated tumor cell debris, and respond to that recognition by binding to tumor cell antigens, proliferating, secreting cytokines or otherwise becoming activated in the presence of antigens/immunogens present on intact cancer cells or debris from a halogenated xanthene-ablated cancer cell.

A second type of tumor-specific immune anticancer components are lymph-soluble cytokines or other proteins such as antibodies that bind to an antigen displayed on a whole tumor cell or chemoablated cell debris or, peptides or sugars in the host's plasma or lymph after halogenated xanthene tumor ablation and maintenance time.

After the maintenance time, a tumor-specific immune anticancer component is present in the treated host in an amount that is significantly greater than before administration of the intralesional halogenated xanthene chemoablative pharmaceutical composition to the tumor of the host animal. Significantly enhanced concentrations of a lymph-soluble cytokine such as IL-2, TNF-α, LT, GM-CSF, IFN-γ and HMGB1, of the immune cell types discussed above or other tumor-specific immune anticancer component after halogenated xanthene tumor ablation and maintenance can be readily assayed in blood or lymph or lymphoid tissue by standard techniques reported in the literature and compared to amounts present in the blood or lymph or lymphoid tissue, respectively, prior to halogenated xanthene tumor ablation. Significant enhancement of the concentration of lymph-soluble cytokine or an immune cell type is determined by an increase that is statistically significant at least at the 90 percent confidence level ($p<0.1$), and preferably at the 95 percent confidence level ($p<0.05$).

Peripheral whole blood is typically utilized to provide white blood cells for culture and preferential enrichment. Thus, peripheral whole blood is typically separated into fractions by Ficoll® gradient centrifugation. Three layers are typically formed with a top layer of plasma (including cytokines and antibodies), followed by a buffy coat layer of white blood cells and a bottom fraction of polymorphonuclear cells (such as neutrophils and eosinophils) and erythrocytes (red blood cells; RBCs).

Of the white cells, peripheral blood mononuclear cells (PBMCs), blood cells having a round nucleus (as opposed to a lobed nucleus) or no nucleus like a platelet, are of particular interest here. Illustrative PBMCs include lymphocytes and monocytes (macrophages). The lymphocyte population consists of T cells (e.g., $CD4^+$ and $CD8^+$ cells, about 75%), B cells and NK cells (are about 25% combined). White blood cells cryopreserved in 5% DMSO and 6% pentastarch (about 50% hydroxyethylated starch) can be stored for at least 7 years according to Stroncek et al., *Transfusion* 51(12):2647-2655 (2011).

Following whole blood separation, PBMCs can be collected, cultured and multiplied, and the plasma can be used to provide an assay of antibody and/or cytokine biomarker concentration relative to a pre-ablation concentration of the selected biomarker. Preferred lymphoid tissues are cells from one or more lymph nodes that are preferably proximal to the site of the chemoablated tumor, from splenic tissue or tissue from the thymus or from ablated or untreated tumor lesions.

In vitro culturing and preferential expanding the induced immune anticancer components present in a sample such as a lymphoid tissue sample provides a composition of enriched tumor-specific immune anticancer agents. Those enriched tumor-specific immune anticancer agents can primarily include enhanced numbers of PBMCs such as T cells (e.g., $CD8^+$ T cells and $CD4^+$ T cells), monocytes (macrophages) and NK cells that themselves can be used to augment the host animal's immune response to the ablated tumor tissue. Usual cell proliferation techniques separate the cellular portions from the growth medium-soluble portions that include cytokines and antibodies, with the latter often being discarded.

Cultivation and preferential expansion of B cells, T cells, NK cells, dendritic cells and other antigen-presenting cells (APCs) can lead to the enhanced production of antibodies as well as cytokines. Enhanced quantities of cytokines such as IL-2, TNFα, LT, GM-CSF, and IFN-γ and other proteins such as HMGB1 that can augment the immune response produced by the proliferating cells can be obtained from the growth medium if desired by known separation techniques such as column chromatography and/or affinity chromatography.

Similar processes are applicable to in vitro culturing and preferentially expanding an equivalent group of tumor-specific immune anticancer components present in a tumor tissue sample.

The phrase "preferentially expanding" and its grammatically appropriate similar phrases are used here to describe increasing the numbers of one or more particular cell types relative to other cell types whose numbers are not increased. That preferential expansion (enrichment) is also used to relate to an increase in relative concentration of an anti-cancer proteinaceous compound such as a cytokine or anti-tumor antibody secreted by the tumor-specific immune anticancer cells. This expansion (enrichment) in one or both of cell number and cytokine concentration is carried out in vitro or ex vivo, rather than in the body of the animal host (in vivo).

These increased number of immune cells and/or concentration of anti-cancer proteinaceous compound such as a cytokines or antibody can be easily measured by well-known assays as is illustrated herein. The enhancement in immune cell numbers and/or cytokine concentration after the in vitro (ex vivo) preferential expansion is statistically significant relative to the concentration in the removed body sample. The composition resulting from the preferential expansion is referred to herein as an enriched tumor-specific immune anticancer agent composition.

A preparation of enriched tumor-specific immune anticancer agent composition is usually not useful "as is" for reintroduction into the original host animal or introduction into another animal due to an inappropriate concentration of the enriched tumor-specific immune anticancer agents, the salt content, osmolality, pH value or other factors such as the presence of heterologous mitogens. As a consequence, an enriched tumor-specific immune anticancer agent composition is adjusted to form an immunologically-effective enriched tumor-specific immune anticancer agent preparation.

A contemplated immunologically-effective enriched tumor-specific immune anticancer agent preparation has an appropriate, immunologically-effective concentration of enriched tumor-specific immune anticancer agents dissolved or dispersed in a pharmaceutically acceptable diluent. That composition also contains a parental injection-appropriate salt content, osmolality and pH value, and is free of unwanted ingredients such as heterologous mitogens. Specifics of such injectable compositions can be found in the literature such as Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980, and include those described hereinafter for a chemoablating pharmaceutical composition containing a tumor-ablating effective amount of a contemplated halogenated xanthene compound.

An immunologically-effective enriched tumor-specific immune anticancer agent composition can be administered back to the animal from which the body sample was originally obtained (reintroduced) to provide an immunological boost to an intralesional treatment. Such an immunologically-effective enriched tumor-specific immune anticancer agent composition can also be administered to another (second) immunologically appropriate syngeneic animal host, usually after receiving myeloablative chemotherapy.

Such an enriched tumor-specific immune anticancer agent composition or an immunologically-effective enriched tumor-specific immune anticancer agent preparation can be stored (banked) for later use as by refrigerating, or freezing, as is well-known in the blood banking and cell preservation arts. The tumor-specific immune anticancer agents present in that composition or preparation can also be further cultured to produce desired cytokines, e.g., lymphokines, or antibodies or other immune anticancer agents produced within the cell preparation.

In the U.S., certain standards are set for the collection and processing of each blood product. "Whole blood" (WB) is the proper name for one defined product, specifically unseparated venous blood with an approved preservative added. Most blood for transfusion is collected as whole blood. Autologous donations are sometimes transfused without further modification; however, whole blood is typically separated (via centrifugation) into its components, with red blood cells (RBC) suspended in solution being the most commonly used product.

Units of WB and RBC are both kept refrigerated at 33.8 to 42.8° F. (1.0 to 6.0° C.), with maximum permitted storage periods (shelf lives) of 35 and 42 days respectively. RBC units can also be frozen when buffered with glycerol, but is rarely done. Frozen red cells are given an expiration date of up to ten years and are stored at −85° F. (−65° C.).

The less-dense blood plasma is made into a variety of frozen components, and is labeled differently based on when it was frozen and what the intended use of the product is. Plasma contains antibodies and cytokines as well as other dispersed proteins, peptides, sugars and salts.

If the plasma is frozen promptly and is intended for transfusion, it is typically labeled as fresh frozen plasma. If it is intended to be made into other products, it is typically labeled as recovered plasma or plasma for fractionation.

As noted in U.S. Pat. No. 8,153,120 to Sheikh et al. and its division, U.S. Pat. No. 8,540,982, antigen presenting cells (APCs) and dendritic cells (DCs) can be isolated by routine methodologies that are readily available in the art. An exemplary suitable methodology for isolation of DCs is disclosed in U.S. Pat. No. 5,976,546, U.S. Pat. No. 6,080,409, and U.S. Pat. No. 6,210,662.

Briefly, buffy coat cells can be prepared from peripheral blood. Cells can be harvested from leukopacs, layered over columns of organosilanized colloidal silica (OCS) separation medium (prepared as described by Dom in U.S. Pat. No. 4,927,749) at a density 1.0770 g/ml, pH 7.4, 280 mOsm/kg $H_2O$) in centrifuge tubes or devices. The OCS medium is preferably prepared by reacting and thus blocking the silanol groups of colloidal silica (approximately 10-20 nm diameter particles) with an alkyl tri-methoxy silane reagent.

Similarly, U.S. Pat. No. 8,597,946 to Mule et al. teaches preparation of DCs from an apheresis system followed by centrifugation on Ficoll-Hypaque® gradients to provide peripheral blood mononuclear cells (PBMCs). Those cells were then cryopreserved in 70% human AB Serum, 20% X-VIVO™ 15 Hematopoietic Media (Lonza America Inc., Allendale, N.J.) and 10% DMSO. Fresh or cyropreserved PBMCs were then cultured in vitro in the presence of GM-CSF followed by tumor lysate (prepared from irradiated tumor cells) and anti-MARCO antibody.

In one embodiment of the present invention, a contemplated method employs intralesional (IL) injection of a halogenated xanthene into tumor tissue to induce interferon-positive T-cells targeted to endogenous tumor tissue. The induced T-cells are preferably circulating $CD4^+$ T-cells and/or $CD8^+$ T-cells. In another embodiment, the anticancer cells are NK cells. In another embodiment, this method employs the same exposure of tumor tissue to rose bengal to induce dendritic cells, expose tumor antigens, induce antibodies and patient-specific or patient-independent therapeutics such as cytokines.

The peripheral blood aliquot, tumor tissue and/or lymphoid tissue is removed (collected) after the tumor ablation treatment so that the tumor-ablation products and tumor cell antigens (immunogens) migrate to the near-by (proximal), draining lymph nodes (DLNs). Thus, the removal of blood, tumor tissue and/or lymph tissue is preferably carried out about 1 to about 30 days after ablative dose administration, more preferably about 4 to about 90 days after tumor ablation, and most preferably about 7 to about 14 days after ablative dose administration to permit the migration and immune response to the ablation.

In another preferred embodiment, one or more systemic inhibitors of immune system down regulation is administered to the host animal. Preferably, the systemic inhibitor of immune system down regulation is a monoclonal antibody that immunoreacts with one or more of CTLA-4, PD-1, PD-L1 and PD-L2. These monoclonals are exemplified by those named ipilimumab and tremelimumab that bind to CTLA-4; pidilizumab, nivolumab, lambrolizumab and pembrolizumab that bind to PD-1; and BMS-936559, MEDI4736 and atezolizumab(MPDL3280A) that bind to PD-L1.

A systemic inhibitor of immune system down regulation can be administered to the host animal before, after or along with administration of a tumor-ablating amount of a halogenated xanthene. Preferably, that inhibitor administration is carried out after tumor ablation and before collecting the sample that contains induced immune anticancer components from the host animal.

A plurality of immune system down regulation inhibitor administrations can be provided prior to collection of the sample. Two to four such administrations have been successfully used in initial studies. Those administrations are typically separated by about 1 to about 7 days.

The dose of monoclonal antibody inhibitor administered each time is that suggested by the manufacturer for each particular product, as a maximum dose, with doses of about 25 to about 75 percent of the maximum dose being more usually administered. When administered separately, in the absence of tumor-ablating xanthene compound, a monoclonal antibody inhibitor is illustratively administered as follows: ipilimumab (anti-CTLA-4) is suggested in the Physicians' Desk Reference, 69 ed, PDR Network, Montvale, N.J. (2014) [PDR] to be administered at 3 mg/kg every 3 weeks for a total of four doses; pembrolizumab (anti-PD-1) is suggested to be administered at 2 mg/kg every 3 weeks [PDR]; Phase I/II dose-escalation studies using nivolumab (anti-PD-1) administered at 0.1 to 10 mg/kg every two weeks for 96 weeks [Topalian et al., *J Clin Oncol* 32:1020 (2014)]. Each administration was carried out intravenously in an aqueous composition similar to those discussed below.

Pharmaceutical Compositions

A pharmaceutical composition containing a tumor-ablating effective amount of a contemplated halogenated xanthene compound or a pharmaceutically acceptable salt thereof dissolved or dispersed in a pharmaceutically acceptable diluent is utilized in a contemplated method. Such a composition, often referred to herein as a chemoablative composition, is administered in vivo into a tumor (intralesionally) in a mammalian host animal to induce the animal host's immune system to produce induced immune anticancer components.

That pharmaceutical composition is preferably an aqueous composition suitable for intralesional injection that includes about 1% or more of the halogenated xanthene such as rose bengal (i.e., PV-10) or a similar solution of another halogenated xanthene or mixtures thereof. A pharmaceutically acceptable salt of the halogenated xanthene such as the disodium or dipotassium salt can be used in this composition.

An amount of halogenated xanthene greater than about 1% (w/v) to about 3% (w/v) is particularly useful for chemoablative use, because lower concentrations are generally insufficient to directly elicit destruction (ablation) of target tissues. Consequently, in a preferred embodiment, the concentration of halogenated xanthene is about 3% (w/v) to about 20% (w/v), and more preferably about 3% (w/v) to about 10% (w/v). In another embodiment, the concentration of halogenated xanthene is at about 10% (w/v) to about 20% (w/v). In still another embodiment, the concentration of halogenated xanthene is about 10% (w/v).

Typical dosages of a chemoablative pharmaceutical composition administered by IL or other parenteral administration are about 0.1 mL/cc lesion volume to about 2 mL/cc lesion volume, more preferably about 0.25 mL/cc to about 0.75 mL/cc lesion volume, and most preferably about 0.5 mL/cc lesion volume. Such doses typically correspond to a patient dose of about 10 mg to about 1500 mg of halogenated xanthene (which are significantly higher than those doses used for diagnostic liver assays).

A contemplated pharmaceutical composition is also highly stable and can be readily handled both in manufacture and use. These preferred concentrations are expressed in weight to volume (w/v), however, concentration in weight to weight (w/w) is substantially equivalent.

A preferred halogenated xanthene useful herein is a compound of Formula 1, below, in which $R^1$ is independently F, Cl, Br, I, H or $C_1$-$C_4$ alkyl; $R^2$, $R^3$, $R^4$, and $R^5$ are independently Cl, H or I wherein at least one substituent of $R^2$, $R^3$, $R^4$, and $R^5$ is I and at least one is Cl or H; $R^6$ is independently H or $C_1$-$C_4$ alkyl; $R^{11}$ is H or $C_1$-$C_4$ alkyl; $R^{12}$ is H or $C_1$-$C_7$ acyl; and all (a) tautomeric forms; (b) atropisomers, (c) closed lactone forms as depicted in Formula 2, below, (d) enantiomers of lactone forms depicted in Formula 2, and (e) pharmaceutically acceptable salts thereof.

FORMULA 1

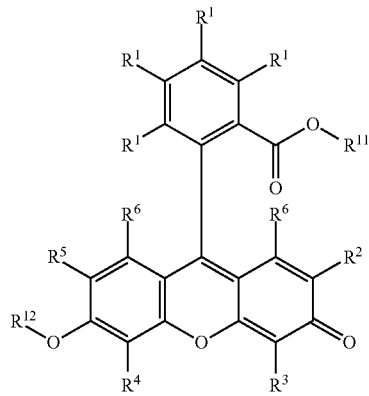

FORMULA 2

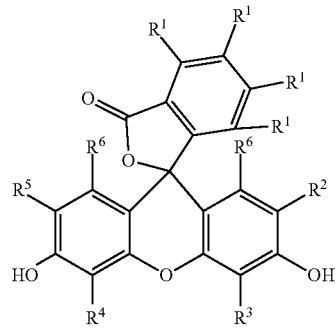

A preferred chemoablative halogenated xanthene used is preferably one or more of rose bengal (4,5,6,7-tetrachloro-2',4',5',7'-tetraiodofluorescein), erythrosin B, phloxine B, 4,5,6,7-tetrabromo-2',4',5',7'-tetraiodofluorescein, 2',4,5,6,7-pentachloro-4',5',7'-triiodofluorescein, 4,4',5,6,7-pentachloro-2',5',7'-triiodofluorescein, 2',4,5,6,7,7'-hexachloro-4',5'-diiodofluorescein, 4,4',5,5',6,7-hexachloro-2',7'-diiodofluorescein, 2',4,5,5',6,7-hexachloro-4',7'-diiodofluorescein, 4,5,6,7-tetrachloro-2',4',5'-triiodofluorescein, 4,5,6,7-tetrachloro-2',4',7'-triiodofluorescein, 4,5,6,7-tetrabromo-2',4',5'-triiodofluorescein, and 4,5,6,7-tetrabromo-2',4',7'-triiodofluorescein dissolved or dispersed in a pharmaceutically acceptable diluent. Rose bengal is a particularly preferred halogenated xanthene.

Because a contemplated chemoablative pharmaceutical composition is typically intended for parenteral administration as by injection into a tumor [intralesional (IL) administration], such a composition should contain an electrolyte, and preferably have approximately physiological osmolality and pH value. A preferred concentration of singly charged electrolyte ions in a chemoablative pharmaceutical composition is about 0.5 to about 1.5% (w/v), more preferably at about 0.8 to about 1.2% (w/v), and most preferably at a concentration of about 0.9% (w/v). The about 0.9% (w/v) concentration is particularly preferred because it corresponds to an approximately isotonic solution. In a further preferred embodiment, the electrolyte in a chemoablative pharmaceutical composition is sodium chloride.

Electrolytes at such levels increase the osmolality of the IL chemoablative pharmaceutical composition. Thus, as an alternative to specifying a range of electrolyte concentrations, osmolality can be used to characterize, in part, the electrolyte level of the composition. It is preferred that the osmolality of a composition be greater than about 100 mOsm/kg, more preferably that the osmolality of the composition be greater than about 250 mOsm/kg, and most preferably that it be about 300 to about 500 mOsm/kg.

It is preferred that the pH value of the chemoablative pharmaceutical composition be about 4 to about 9, to yield maximum solubility of the halogenated xanthene in an aqueous vehicle and assure compatibility with biological tissue. A particularly preferred pH value is about 5 to about 8, and more preferably between about 6 to about 7.5. At these pH values, the halogenated xanthenes typically remain in dibasic form, rather than the water-insoluble lactone that forms at low pH values.

The pH value of the chemoablative pharmaceutical composition can be regulated or adjusted by any suitable means known to those of skill in the art. The composition can be buffered or the pH value adjusted by addition of acid or base or the like. As the halogenated xanthenes, or physiologically acceptable salts thereof, are weak acids, depending upon halogenated xanthene concentration and/or electrolyte concentration, the pH value of the composition may not require the use of a buffer and/or pH modifying reagent. It is especially preferred, however, that the composition not contain any buffer, permitting it to conform to the biological environment once administered.

As disclosed in U.S. Pat. No. 9,107,887, whose disclosures are incorporated herein by reference, a chemoablative pharmaceutical composition is preferably administered intralesionally (IL) into at least one cancerous solid tumor such as melanoma, prostate, breast, bladder, renal, pancreatic, colon, colorectal, gall bladder, primary or metastatic liver cancer (hepatocellular carcinoma), and small cell and non-small cell lung cancer. A preferred embodiment of the present invention is illustratively described here with particular relevance to melanoma.

Because a contemplated pharmaceutical composition is intended for IL administration, which is an intracorporeal (parenteral) route, it is further preferred that it be sterile, such as required for conformance to U.S. Pharmacopeia (USP) <71>, and further that it contains negligible levels of pyrogenic material, such that it conforms to USP <85> (limulus amebocyte lysate assay) or to USP <151> (rabbit pyrogen test), or to substantially equivalent requirements, at a pyrogen or endotoxin level equivalent to not more than (NMT) 10 endotoxin units (EU) per mL. Moreover, the pharmaceutical composition should conform to requirements limiting content of particulate matter as defined in USP <788> (i.e., NMT 3000 particulates greater than 10 microns in size, and NMT 300 particulates greater than 25 microns in size, per container) or substantially equivalent requirements. Each of these references from the USP is incorporated herein by reference.

An animal host having a cancerous tumor (in need of treatment) to which a pharmaceutical composition containing a contemplated halogenated xanthene compound is administered and from which a sample comprising one or more of an aliquot of peripheral blood, tumor tissue or lymphoid tissue that contains induced immune anticancer components is removed can be substantially any mammal. Illustrative mammalian animal hosts include a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like.

Where in vitro mammalian cell contact is contemplated such as in culture and preferential expansion, a tissue culture of cancerous cells from an illustrative mammal is often utilized, as is illustrated hereinafter.

If desired, an excised tumor from the host animal can be administered a chemoablating pharmaceutical composition tumor-ablating amount of a halogenated xanthene compound that is dissolved or dispersed in a pharmaceutical composition in vitro and then cultured (maintained) in vitro as discussed previously to form induced immune anticancer components that are thereafter administered to a tumor in the host animal to elicit a further immune response.

A contemplated composition often need be administered to a given tumor only once, but can be administered a plurality of times to that tumor over a period of several days or weeks, or months. Separate tumors in the animal host can each receive its own one or more administrations.

A contemplated pharmaceutical composition of a halogenated xanthene compound is preferably administered parenterally by injection directly into a cancerous tumor to be treated. The term parenteral as used herein includes intravascular and intralesional injection or infusion techniques as well as subcutaneous, intraperitoneal or similar modes of administration. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

For injectable preparations, for example, sterile injectable aqueous suspensions can be formulated according to the known art using a suitable dispersing or wetting compound and suspending materials. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an active component or sterile solution of the active component in solvents comprising water, ethanol, DMSO or propylene glycol are examples of liquid compositions suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Preferably, the pharmaceutical composition is in unit dosage form. In such form, the composition is divided into unit doses containing appropriate quantities of the halogenated xanthene tumor-ablative compound. The unit dosage form can be a packaged preparation, the package containing discrete quantities of the preparation, for example, in vials or ampules.

Disscusion

IL therapy is an alternative to surgical intervention for exemplary melanoma patients. However, few intralesional compounds have induced a systemic response and regression of bystander, untreated lesions. Some existing compounds incorporated in IL therapy are not ideal.

For example, BCG is associated with a high number of complications including anaphylactic reaction, seroconversion and systemic infection [Abbott et al., *Surg Clin North Am* 94:1003-1015, viii(2014)]. BCG also failed to prove effective in one of largest studies in melanoma treatment [Agarwala et al., *Cancer* 100:1692-1698 (2004). Intralesional IL-2 was unable to elicit a systemic tumor-specific response although it led to complete responses in 62.5% of treated melanoma patients [Radny et al., *Br J Cancer* 89:1620-1626 (2003)].

As a new candidate for IL therapy, PV-10 has demonstrated the ability to cytolyse tumor cells without significant adverse side effects. A recent phase 2 clinical trial of PV-10 for treatment of metastatic melanoma showed an overall response rate of 50% and a complete response rate of 26% in up to 10 targeted lesions with moderate side effects [Thompson et al., *Ann Surg Oncol.* 22:2135-2142 (2015)]. In treated patients, 8% had no evidence of disease after 52 weeks.

In a phase 1 study, there was a 91.7% overall lesion response (10 out 11 injected lesions regressed within 14 days of treatment). Both of these trials demonstrated that untreated lesions also regress (23% and 83%, respectively). These data suggest that there is a tumor-specific systemic response of bystander tumors triggered by IL PV-10.

The mechanism of PV-10-induced tumor-specific immunity remains largely unknown. Previous studies in B16 and MT-901-bearing mice demonstrated the activation of tumor-specific T cells after IL injection of PV-10 [Toomey et al., *PloS one* 8:e68561 (2013)]. In another study, the infiltration of lymphocytes into melanoma lesions of patients treated with IL PV-10 was examined. However, lymphocytes could not be detected in ablated lesions of some patients whose lesions diminished after IL PV-10. [Sarnaik et al., ASCO Annual Meeting, Abstract 9028, presented Jun. 2, 2014]. This may be due to the cytotoxicity of PV-10 or the decrease in tumor size following treatment. Unexpectedly, increased numbers of circulating $CD8^+$ and $CD4^+$ T cells and increased IFN-γ responses against autologous tumor or HLA-matched tumor were measured in the peripheral blood of these same patients.

Figure 4B:
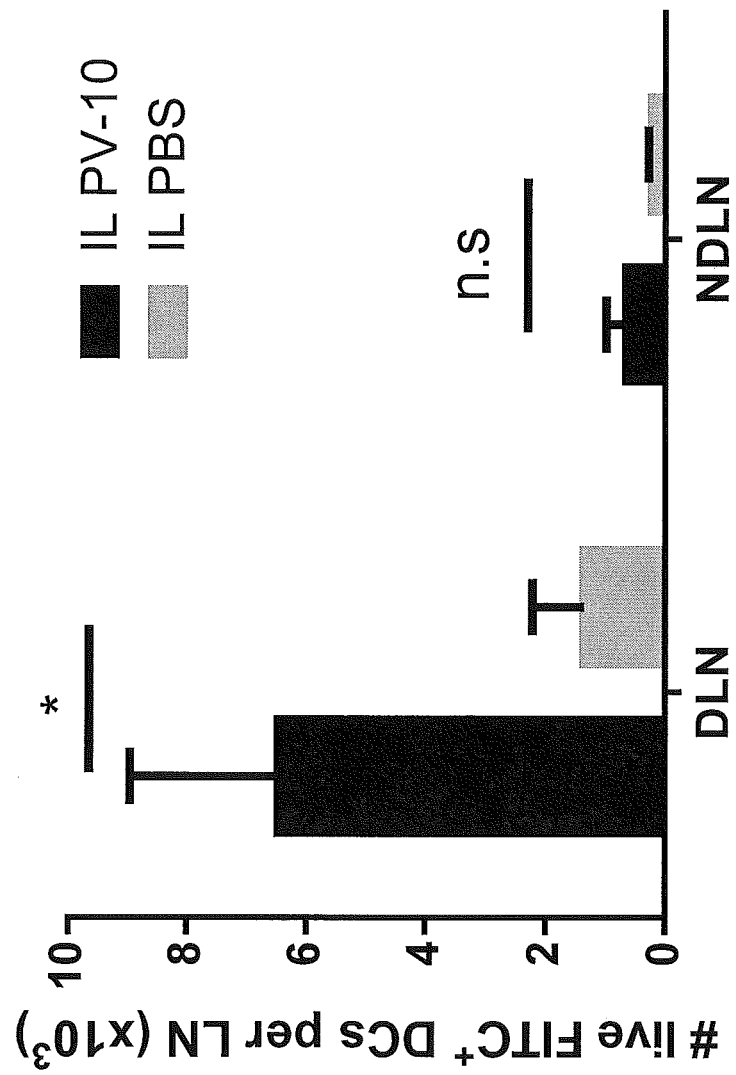
FIG. 4B is a graph showing results for $FITC^+$ DCs from DLNs or NDLNs after FITC-OVA was injected i.t. 4 hours after PV-10 treatment as measured by flow cytometry after 18 hours. These data are presented as mean±SEM from three independent studies (n=4 mice/group).

Using mice bearing OVA-expressing M05 melanoma, it is shown hereinafter that there are increased tumor-specific T cells (OT-1 T cells) after IL PV-10 treatment and more T cells with memory characteristics. Adoptive transfer of OT-1 T cells in PV-10-treated M05-bearing mice showed that OT-1 T cells proliferated more rapidly in response to tumor antigens. Those effects can be partially explained by increased infiltration of dendritic cells (DCs) from the tumor into draining lymph nodes (DLNs) and by DC activation (FIG. 4).

HMGB1 protein plays both tumor-promoting and tumor-suppressing roles during tumor development and cancer therapy. On one hand, HMGB1 dysfunction is associated with each of the hallmarks of cancer and it can decrease anti-tumor immunity [Kusume et al., *Pathobiology* 76:155-162 (2009); Liu et al., *Leukemia* 25:23-31 (2011)]. Increased levels of secreted HMGB1 and expression of membrane-bound HMGB1 are detected in the tumor micro-environment [Tang et al., *Biochim Biophys Acta* 1799:131-140 (2010)].

On the other hand, HMGB1 plays anti-tumor roles due to association with the tumor suppressor—retinoblastoma protein [Jiao et al., *Acta Pharmacol Sin* 28:1957-1967 (2007)] or stabilization of genome [Giavara et al., *Curr Biol* 15, 68-72 (2005)]. In gliobastoma multiforme-bearing mice, the local delivery of FMS-like tyrosine kinase 3 ligand (Flt3L) and thymidine kinase leads to tumor regression via release of HMGB1 from dying tumor cells to activate tumor-infiltrating DCs [Curtin et al., *PLoS Med* 6, e10 (2009)]. Blockade of the HMGB1/TLR4 pathway abrogates the tumor-specific immune response upon chemotherapy and radiotherapy via interference of the antigen processing and the cross-presentation ability of DCs [Apetoh et al., *Nature Med* 13:1050-1059 (2007)]. In addition, TIM-3 inhibits the HMGB1-mediated nucleic acid sensor system in DCs, and therefore, can reduce the efficacy of DNA vaccine and chemotherapy [Chiba et al., *Nature Immunol* 13:832-842 (2012)].

In the study discussed below, an increase in the release of HMGB1 in the supernatant of melanoma cells after incubation with PV-10 was measured. These data are consistent with the observation that HMGB1 was passively released from Hela cells that had been treated with rose bengal acetate for 1 hour following photodynamic irradiation [Panzarini et al., *PloS One* 9:e105778 (2014)].

In the Panazarini et al. study, treatment with rose bengal acetate enabled photosensitized Hela cells to become apoptotic and autophagic and to secrete HSP70, HSP90 and HMGB1. In contrast, the present results showed the level of HSP 90 was unchanged and there was less HSP 70 secreted after PV-10 incubation. This discrepancy may be due to the different methods to treat cells and the different analog of rose bengal used.

Moreover, HMGB1 levels in patient serum were increased after IL PV-10. These results are in line with another study that showed increased HMGB1 levels in the serum of cancer patients after chemoradiation therapy [Suzuki et al., *Cancer Res* 72:3967-3976 (2012)]. Thus, Suzuki and colleagues found that the level of HMGB1 in the patients who had antigen-specific T-cell responses was significantly higher than that in the patients without antigen-specific T-cell responses. In their study, the immunohistochemistry analysis of HMGB1 showed that a higher expression of HMGB1 in resected tumor samples was correlated with better survival of patients.

The study below showed that HMGB1 in the supernatant of tumor cells treated with PV-10 was responsible for the up-regulation of CD40 expression on BM-derived DCs and for the increased antigen presentation by DCs. This is consistent with the observation that HMGB1 is important for activation of human myeloid DCs and plasmacytoid DC [Dumitriu et al., *J Immunol* 174:7506-7515 (2005); Messmer et al., *J Immunol* 173:307-313 (2004)].

Maturation of DCs with CD40 signaling is crucial for presenting tumor antigens and priming $CD8^+$ T cells for cytotoxic activity after migration into tumor tissues [Watanabe et al., *J Immunol* 171:5828-5836 (2003)]. Watanabe found that short-term CD40 signaling in DCs augmented DC migration to tumor-DLNs and successfully induced protective immunity. Moreover, HMGB1 has been shown to induce DC response to chemokine ligand 9 (CCL9) and chemokine C-X-C motif ligand 12 (CXCL12) [Dumitriu et al., *J. Leuk Biol* 81:84-91 (2007)] and the HMGB1/RAGE interaction can induce the migration of subcutaneously injected DCs to the DLNs after 24 hours [Manfredi et al., *J Immunol* 180, 2270-2275 (2008)]. This is consistent with our data that IL PV-10 induced an increased number of DCs migrating from the tumor site into the DLNs. The interaction of HMGB1 and the RAGE receptor might also be involved in this process.

The dual function of HMGB1 in cancer depends on the target cells, tumor cell or the immune cells it acts on, the receptors it interacts with and synergy with cytokines. It can be partly explained by the redox state of HMGB1: oxidative HMGB1 from apoptotic cells induces tolerance [Kazama et al., *Immunity* 29:21-32 (2008)]. The redox state of HMGB1 secreted by tumors treated with PV-10 as well as other DAMPs will be investigated, such as uric acid and calreticulin, which are not involved in the study underlying this invention.

This study has shown that IL PV-10 therapy can elicit an enhanced tumor-specific immune response in melanoma patients. In melanoma-bearing mice, IL PV-10 induces necrosis of tumor cells to release HMGB1, which is crucial for DC activation and DC infiltration into DLNs, and thus, to activate tumor-specific T cells. The role of IL PV-10 in the induction of anti-tumor immunity also suggests the possibility of enhancing tumor-specific immune responses in combination with the blockade of immune checkpoint molecules such as CTLA-4, PD-1, PD-L1 and PD-L2.

Results

IL PV-10 Leads to a Systemic Immune Response in Melanoma Patients

To investigate the potential mechanism of IL injection of PV-10 in the treatment of metastatic melanoma, a pilot clinical trial was conducted that included 14 human patients with dermal and/or subcutaneous metastatic melanoma (Table 1, below). The study schema is shown in FIG. 1A. Two study lesions in each patient were sampled by biopsy pre-treatment.

TABLE 1

Demographics of IL PV-10 treated Patients*

| Patient | Age | Gender | Stage | Prior Therapy |
|---|---|---|---|---|
| PV001 | 48 | M | IIIC | Isolated Limb Infusion, IFN |
| PV002 | 81 | F | IIIB | none |
| PV003 | 72 | M | IIIC | Isolated Limb Infusion, ipi |
| PV004 | 77 | F | IIIB | Isolated Limb Infusion, ipi |
| PV005 | 60 | F | IIIC | none |
| PV006 | 77 | M | IV | ipi, nivo |
| PV007 | 59 | F | IV | Isolated Limb Infusion, vem |
| PV008 | 75 | M | IIIC | Isolated Limb Infusion, chemo, ipi, nivo |
| PV009 | 80 | M | IIIC | none |
| PV010 | 86 | F | IIIC | none |
| PV011 | 75 | M | IIIC | none |
| PV012 | 80 | M | IIIB | Isolated Limb Infusion, PEG-IFN |
| PV013 | 86 | F | IIIB | Isolated Limb Infusion, ipi |
| PV014 | 77 | F | IV | Isolated Limb Infusion |
| PV015 | 69 | F | IIIC | none |

*IFN = interferon; PEG-IFN = PEGylated interferon; ipi = ipilimumab; vem = vemurafenib; nivo = nivolumab.

Seven days later [trial day zero (D0)], one of the two lesions was injected with IL PV-10. Seven to fourteen days after PV-10 injection, both sites were completely excised. Biopsy specimens were fixed, stained with hematoxylin and eosin (H&E), and evaluated by a pathologist. Comparisons of pathologic complete response (pCR) in treated and untreated specimens, before and after IL PV-10 injection were made, and the results were confirmed with immunohistochemical staining for the melanoma antigen Melan-A/MART-1 (melA).

Figure 1B:
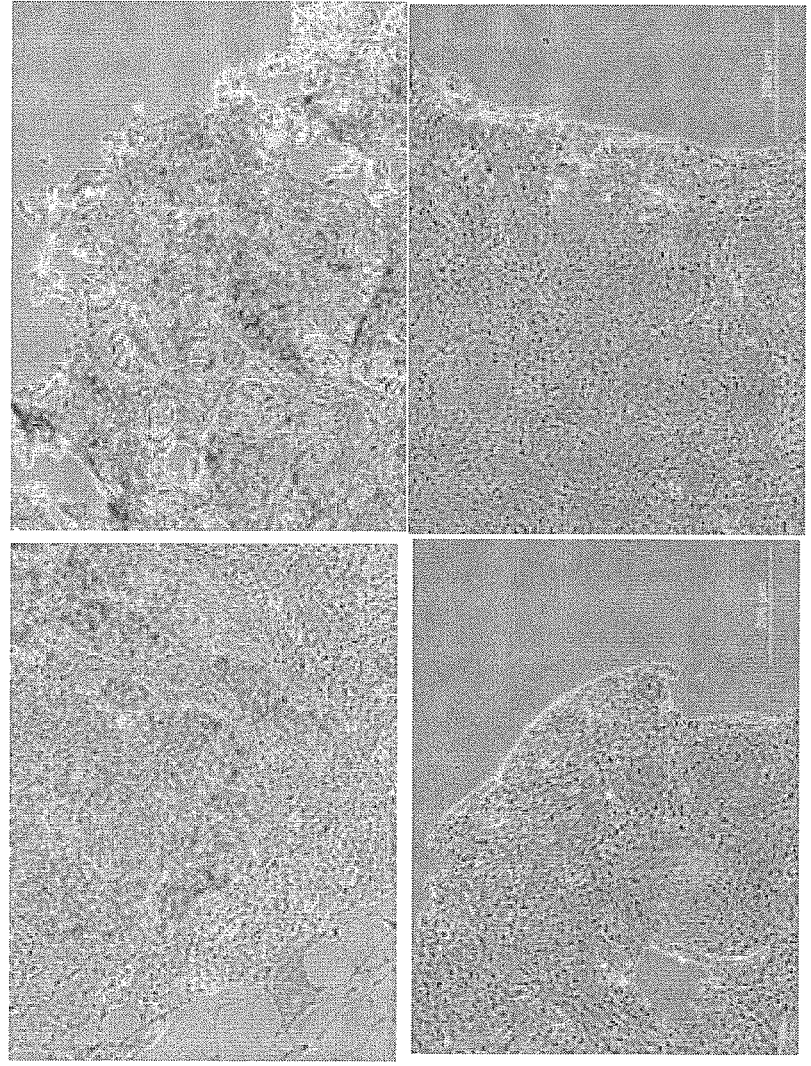
FIG. 1B shows photomicrographs of biopsy samples from a human patient tumor before and 7-14 days after treatment with IL PV-10 on the left, and biopsy samples from a bystander tumor (not injected) at the same times. The cells were stained with antibodies against melA by immunohistochemistry (IHC) to determine the presence of melanoma cells. Significantly reduced tumor cells were noted in the treated and bystander lesion, which were also confirmed by pathologist examination.
Figure 1C:
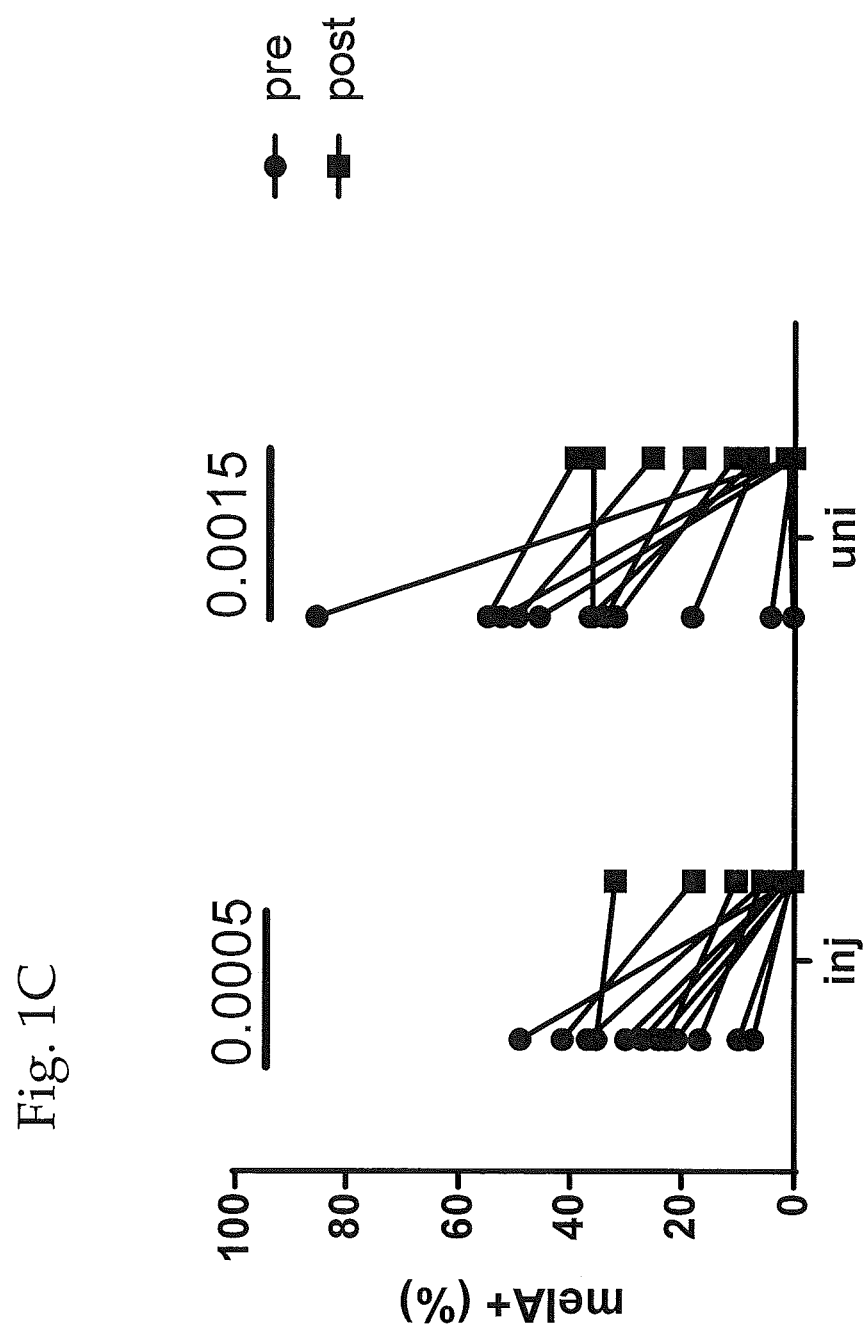
FIG. 1C shows graphs of tumor regressions in injected tumors (inj) and in bystander, non-injected tumors (uni).

As shown in FIG. 1B and FIG. 1C, tumors completely regressed in both the PV-10-treated and bystander lesions. That regression was noted in 4 of 12 patients. Additionally, 11 of 12 patients exhibited at least partial regression of the injected lesion, with a 4-fold decrease in frequency of melA+ cells (mean value: 26.8±3.6 vs 6.4±2.8). Still further, 10 of 12 patients demonstrated partial regression of the bystander lesion with a 3-fold decrease in the proportion of melA+ cells (mean value: 37.5±6.7 vs 12.2±4.1).

These results indicate that IL PV-10 can induce a systemic response secondary to direct ablation by IL PV-10 injection. To examine the role of immune cells, the percentage of CD3$^+$, CD4$^+$ and CD8$^+$ T-cells in PV-10 treated and bystander lesions were compared before and after treatment with IL PV-10. However, very few infiltrates were detected in the lesions when tumor completely regressed, and no significant changes were measured.

Figure 1E:
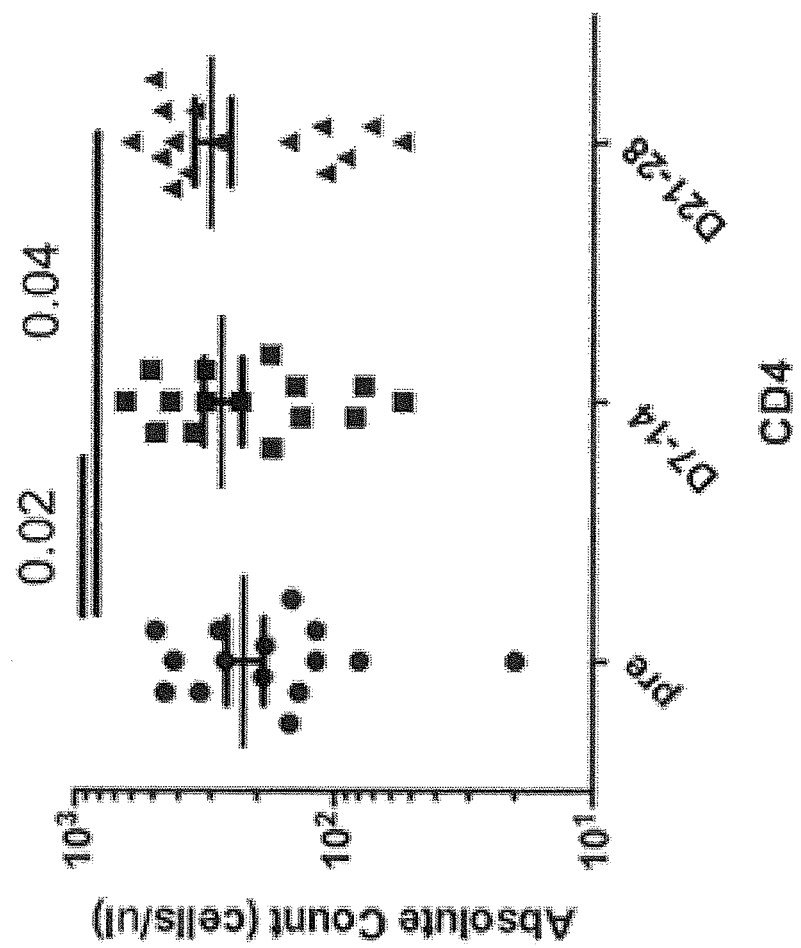
Figure 1F:
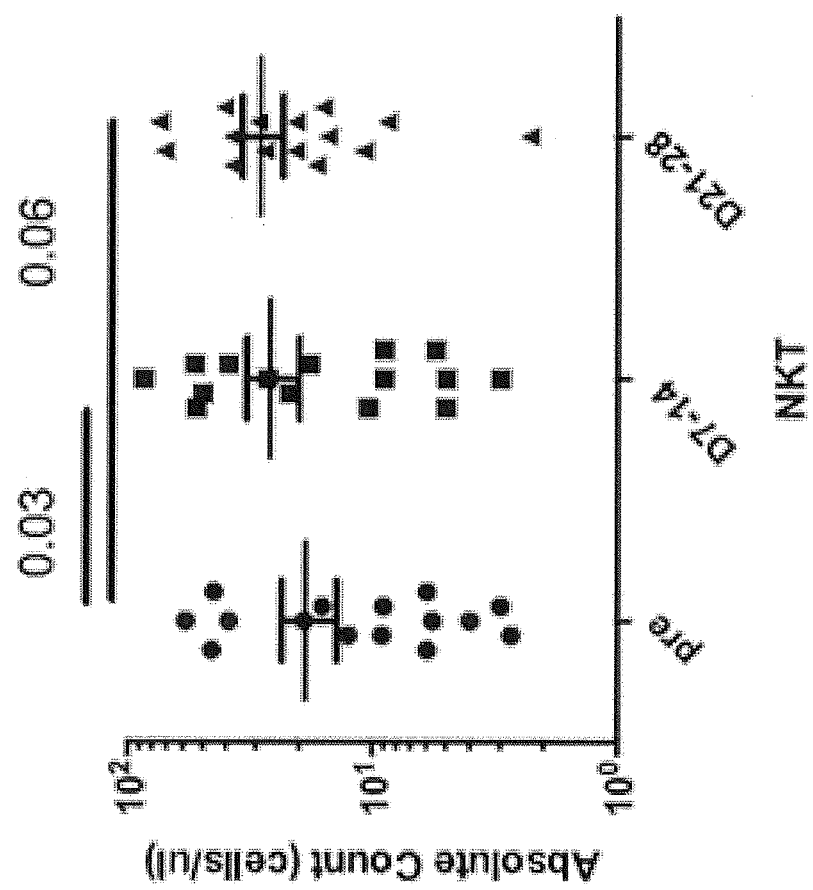

Next, immune cells were examined in the peripheral blood before and after treatment with IL PV-10. There was a significant increase in circulating CD4$^+$ T-cells, CD8$^+$ T-cells, and NK T-cells after PV-10 treatment (FIGS. 1D-1F).

Figure 1G:
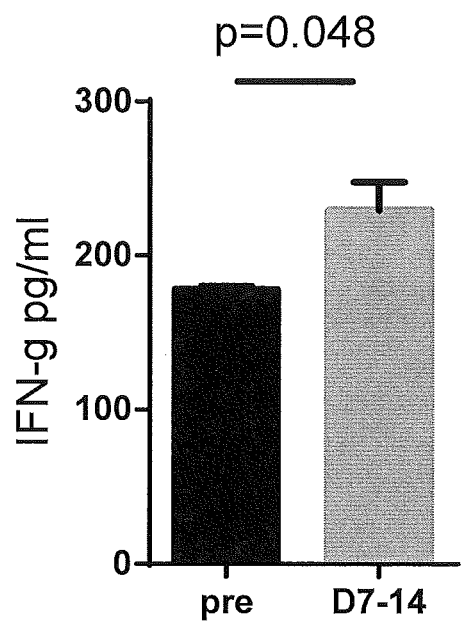
FIGS. 1G, 1H, and 1I illustrate increased IFN-gamma (IFN-g) production from different patients' $CD8^+$ T cells that were purified from PBMCs and re-stimulated with autologous melanoma cells, 526 or 624 or both (FIG. 1G), HLA-matched 624 melanoma cells (FIG. 1H), and HLA-matched melanoma cells (FIG. 1I). Data are shown for values pre-administration (pre), at 7-14 days (D7-14) and 21-28 days (D21-28) post administration. P values were determined by an unpaired Student's t-test. n.s. not significant.
Figure 1H:
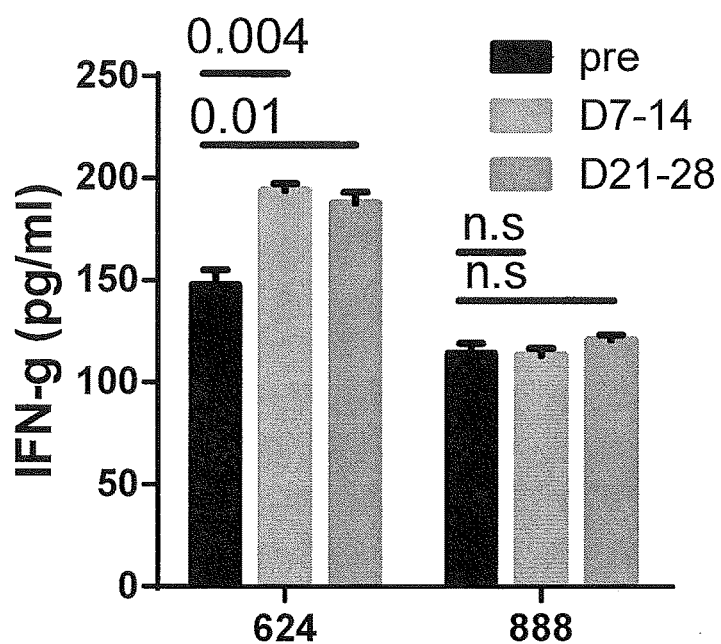
Figure 1I:
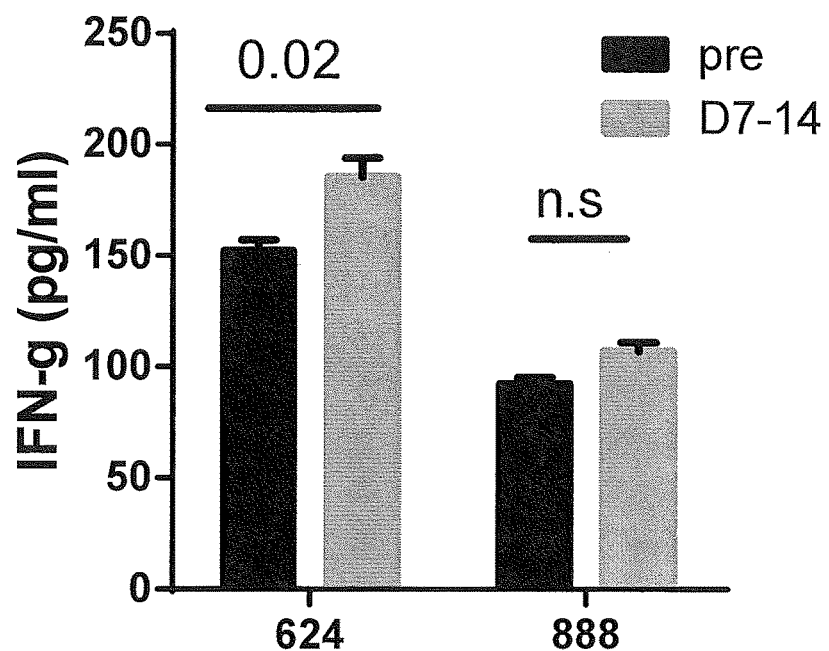

To determine whether the CD8$^+$ T-cells can recognize melanoma tumors, circulating CD8$^+$ T-cells were purified and co-cultured with autologous tumor cells in vitro. There was a significant increase in interferon-gamma (IFN-γ) production after treatment with IL PV-10 (FIG. 1G), indicating that PV-10 treatment enhances tumor-specific immune responses.

As autologous tumors were not available for all patients, HLA-matched tumor cell lines were also used. IFN-γ levels in circulating CD8$^+$ T-cells were increased after IL PV-10 injection in 4 of the 6 patients tested. No change was measured when CD8$^+$ T-cells were co-cultured with HLA-mismatched cell lines. Together, these studies demonstrate that IL PV-10 injection enhances tumor-specific immune responses in melanoma patients.

IL PV-10 in M05-Bearing Mice Elicits a Tumor-Specific Immune Response

Figure 2A:
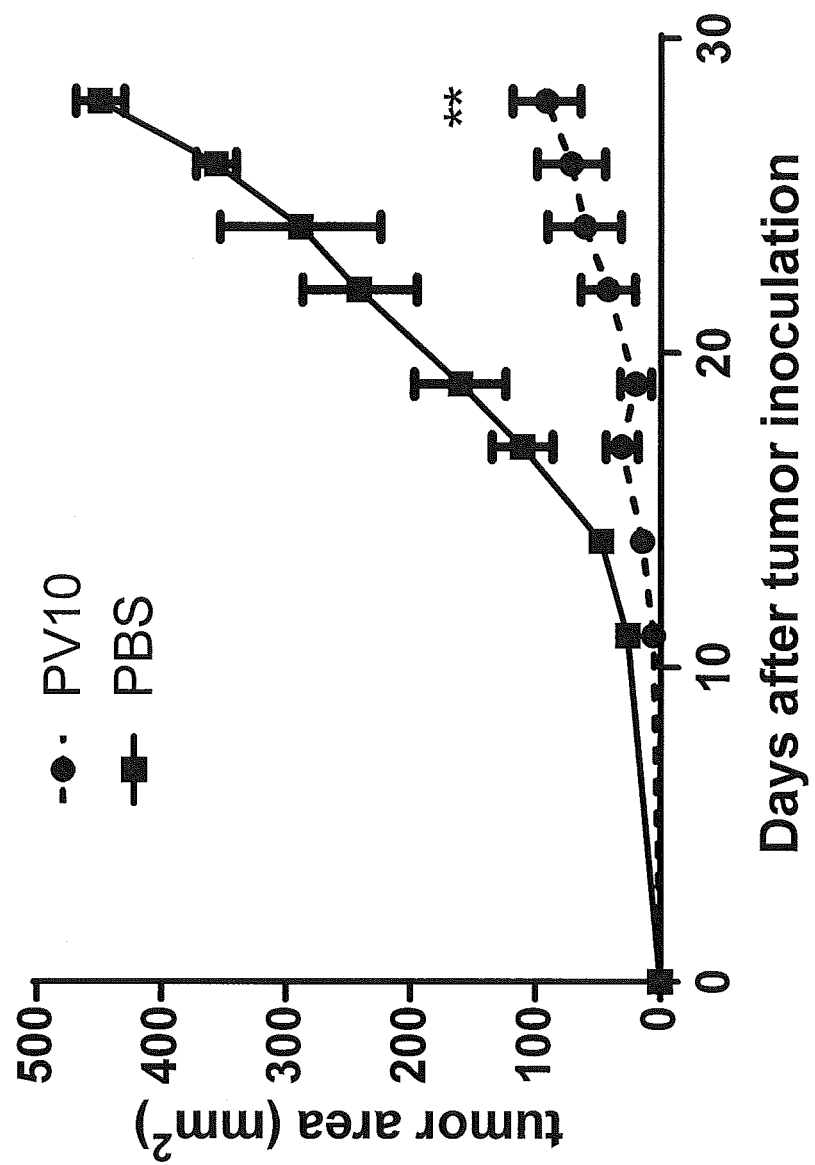
FIG. 2A illustrates tumor growth following injection of $3\times10^5$ OVA-expressing melanoma B16 (M05) cells into one flank of C57BL/6 mice on day 0. Thereafter, 50 µl of PV-10 or PBS were injected IL on days 7 and 17 (n=4).
Figure 2B:
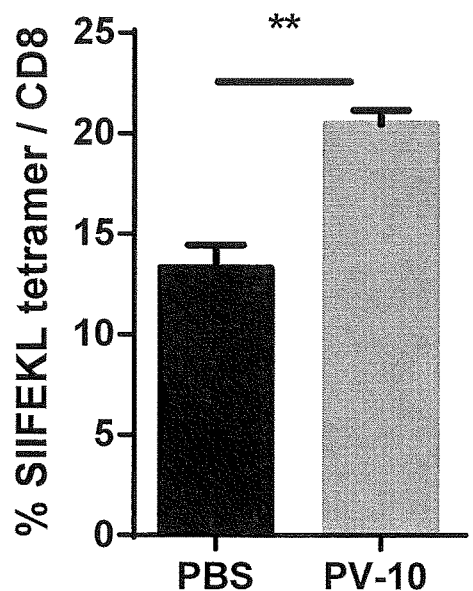
FIG. 2B illustrates the percentage of CD8+ and OVA tetramer-positive cells from draining LNs 8 days after the injections as measured by flow cytometry.
Figure 2C:
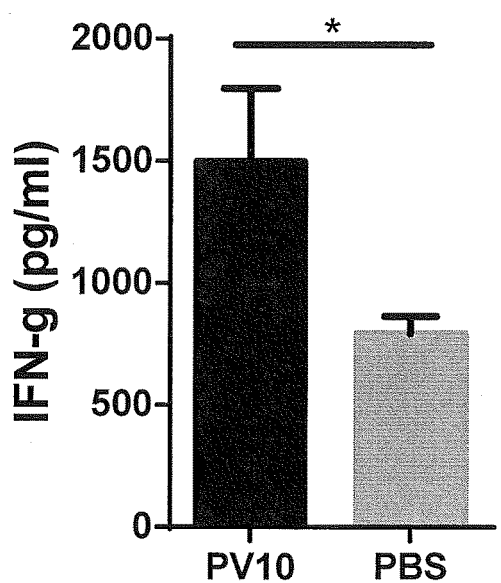
FIG. 2C is a graph showing IFN-γ (IFN-g) secretion from mice re-challenged with $3\times10^5$ M05 cells injected s.c. on the opposite flank on day 7. On day 23, splenocytes were expanded with 20 ng/ml IL-15, IL-21 and 1 µg/ml OVA 257-264 peptide for 7 days and then challenged with MO5 cells. IFN-γ (also IFN-g) production was measured after 48 hours. Data are presented as mean±SEM from three independent studies. *, $p<0.05$, statistically significant versus control;**, $p<0.01$. P values were determined by an unpaired Student's t-test.

To investigate the underlying mechanism of the tumor-specific immune response elicited by PV-10, C57BL/6 mice bearing M05 tumor cells were used. M05 tumor cells are B16 melanoma cells that express the ovalbumin (OVA) protein. Similar to the finding in the B16 model [Toomey et al., PloS one 8:e68561 (2013)], IL injection of PV-10 directly inhibited tumor growth (FIG. 2A). IL PV-10 therapy led to increased OVA-specific CD8$^+$ T-cells in the draining lymph nodes (DLNs) of PV-10-treated mice, compared to the PBS-treated group (FIG. 2B).

To determine whether IL injection of PV-10 induced T cells with memory characteristics, splenocytes from mice treated twice with IL PV-10 were cultured in vitro in the presence of OVA peptide and media supplemented with the cytokines IL-15 and IL-21, which are required for maintaining CD8$^+$ memory T-cells [Nguyen et al., J Leukocyte Biol 87:43-49 (2010)]. T-cells from PV-10-treated mice demonstrated an about 2 fold increase in secretion of IFN-γ in response to M05 cells, compared to T-cells isolated from PBS-treated mice. This indicates that IL PV-10 can induce tumor-specific T-cells with memory characteristics in M05 melanoma-bearing mice.

Figure 3A:
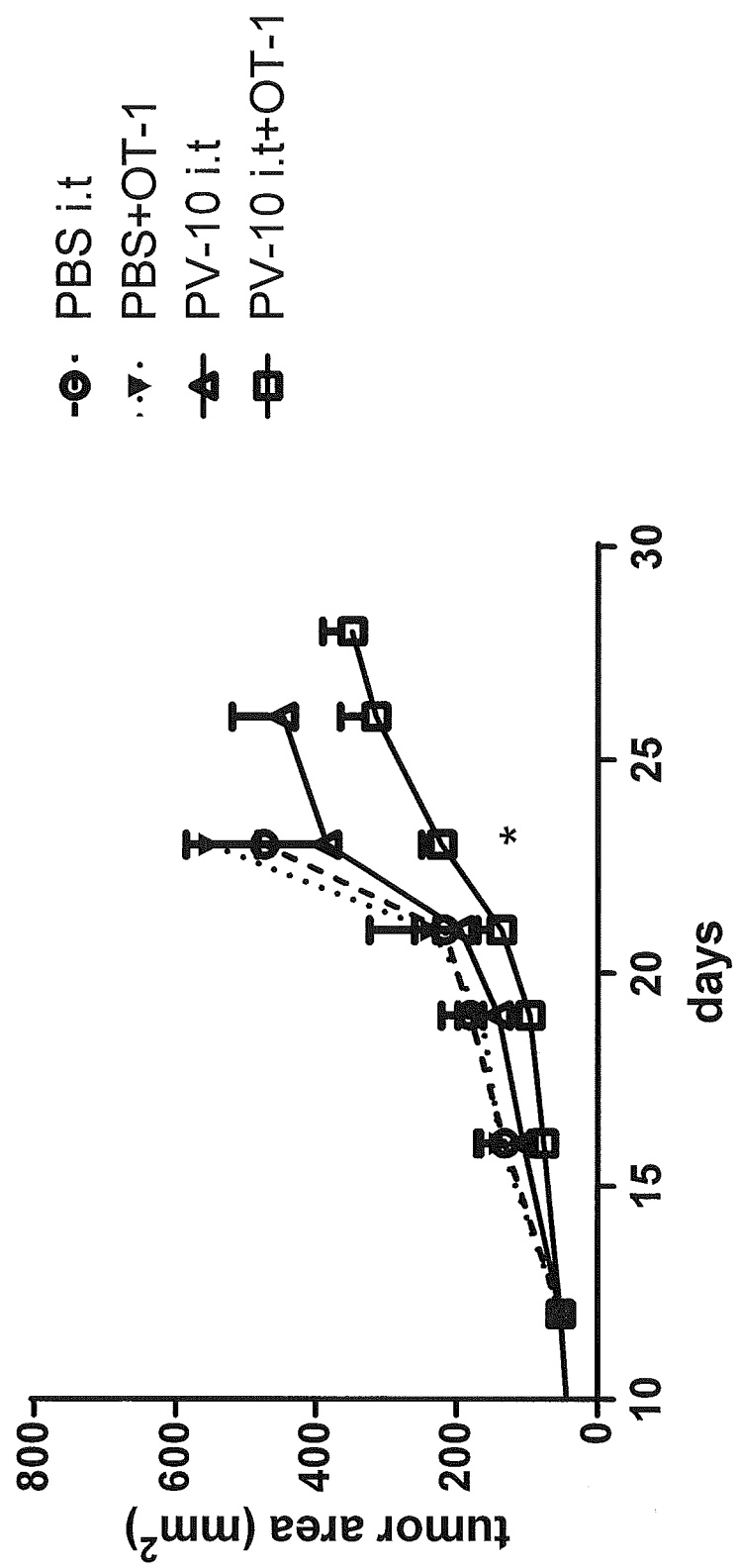
FIG. 3A illustrates that IL PV-10 elicits a tumor-specific inhibiting immune response after $3\times10^5$ OVA-expressing melanoma B16 (M05) cells were injected into one flank of C57BL/6 mice on day 0, and on day 13, 50 µl PV-10 injected IL or PBS injected in the opposite flank, and $2\times10^6$ Cell-tracker® violet-labeled CD45.1 OT-1 T-cells were injected i.v. after 4 hours. $p<0.05$, the PV-10+OT-1 group statistically significant versus the PV-10 group on day 23, unpaired student t-test.
Figure 3B:
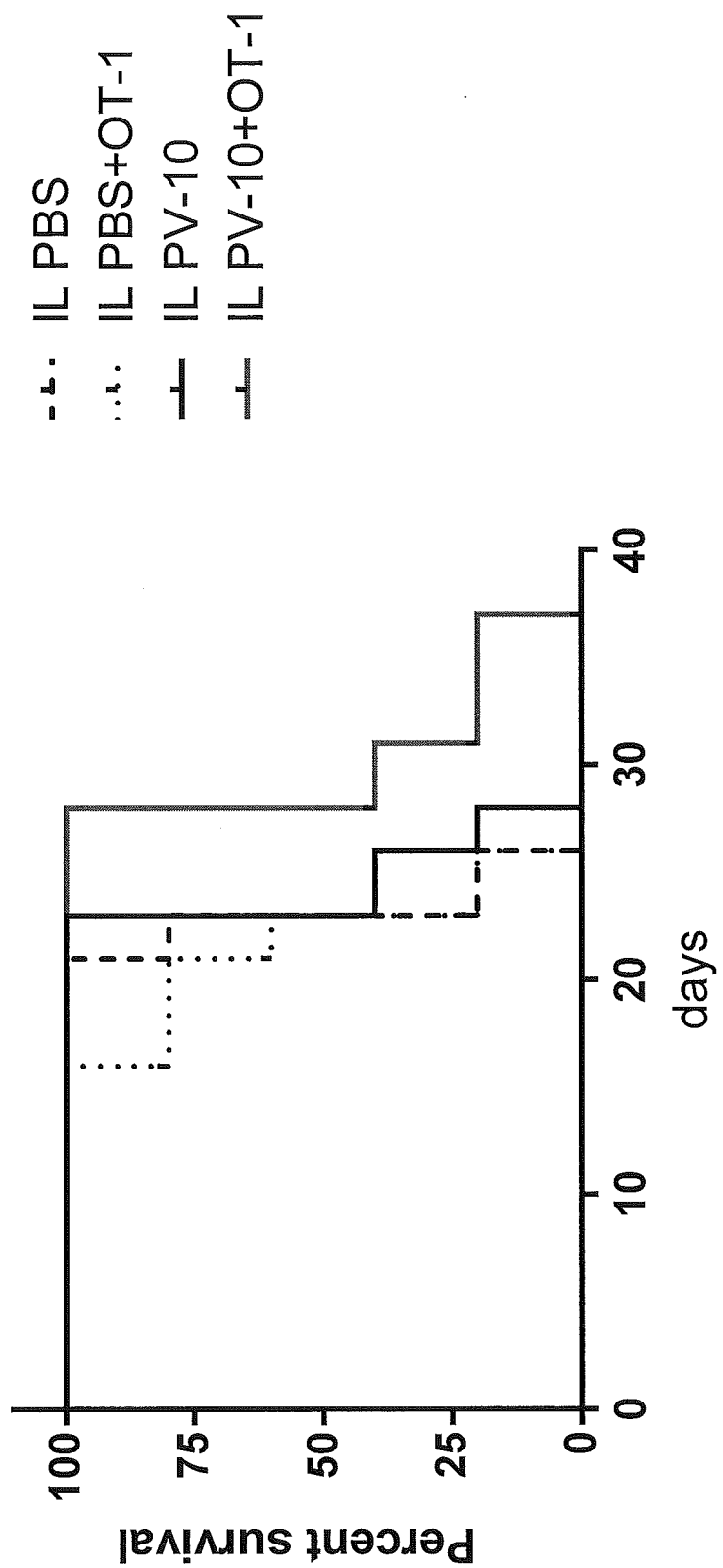
FIG. 3B illustrates the survival of the monitored mice. *, $p<0.05$, **, $p<0.01$. P values were determined by a log-rank test. After 4 days, cells from spleen (FIG. 3C, and FIG. 3D), the tumor (FIG. 3E) and distal LNs (FIG. 3F) were stained with CD45.1 and CD45.2 antibodies. Representative histograms of violet dye dilution show the progenies (daughters) of CD45.1+ T-cells, which have at least one division, after discrimination of dead cells (FIG. 3C). Data are presented as mean±SEM from three independent experiments (n=5 mice/group). *, $p<0.05$, statistically significant versus control; **, $p<0.01$.

To monitor the CD8$^+$ T-cell response after IL PV-10, PV-10 or PBS were injected into M05 melanoma-bearing mice on day 13 and adoptively-transferred OT-1 T-cells that were labeled with Celltracker® violet dye. OT-1 T-cells are CD8$^+$ T-cells that specifically recognize the OVA 257-264 peptide derived from the OVA protein [Rötzschke et al., Eur J Immunol 21(11):2891-2894 (1991); Lipford et al., J Immunol. 150(4):1212-1222 (1993)]. The combination of IL injection of PV-10 and adoptive transfer of OT-1 cells significantly impeded tumor progression and increased survival (FIGS. 3A and B).

Figure 3C:
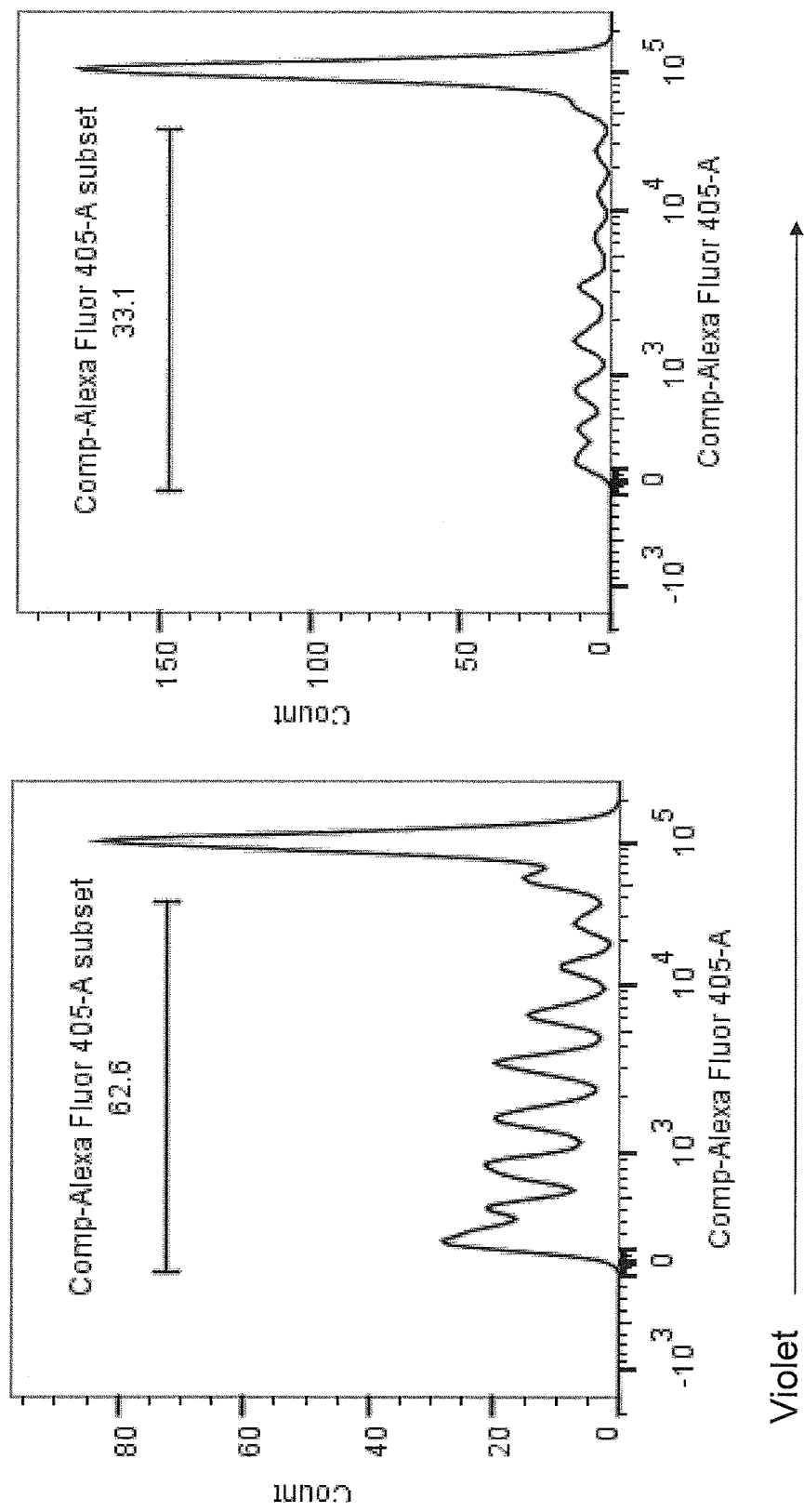
Figure 3D:
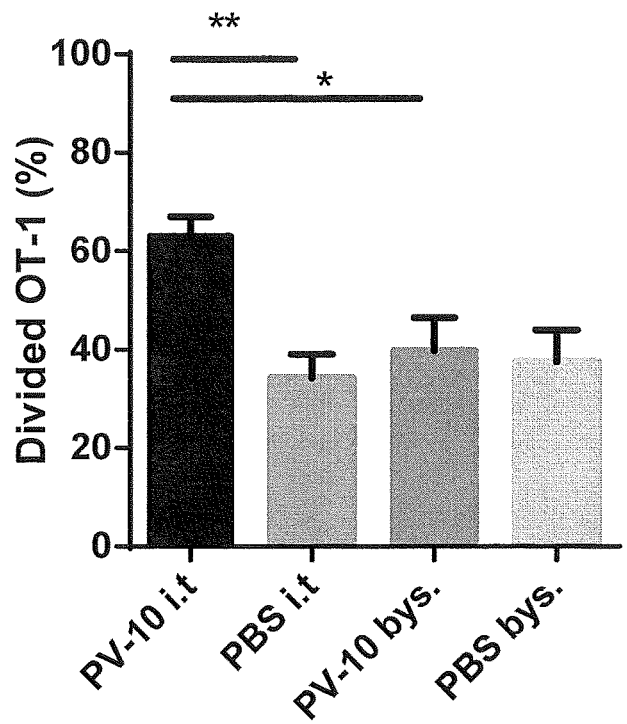
Figure 3E:
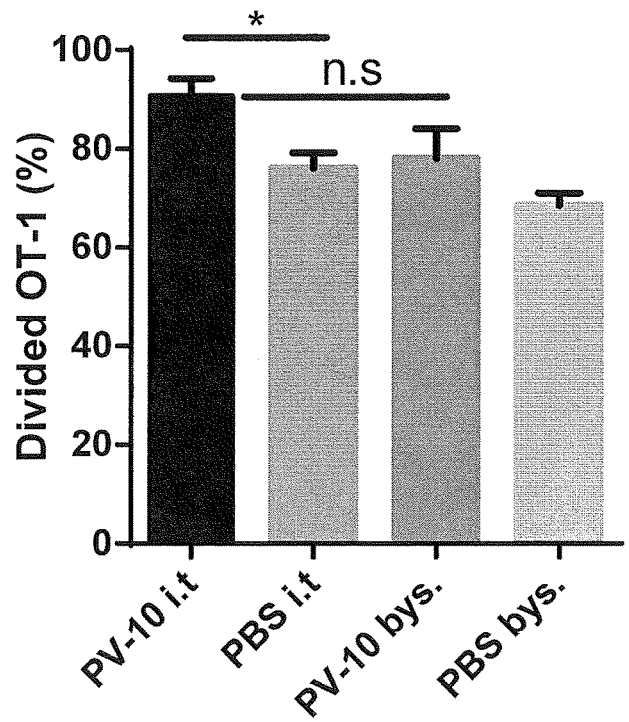
Figure 3F:
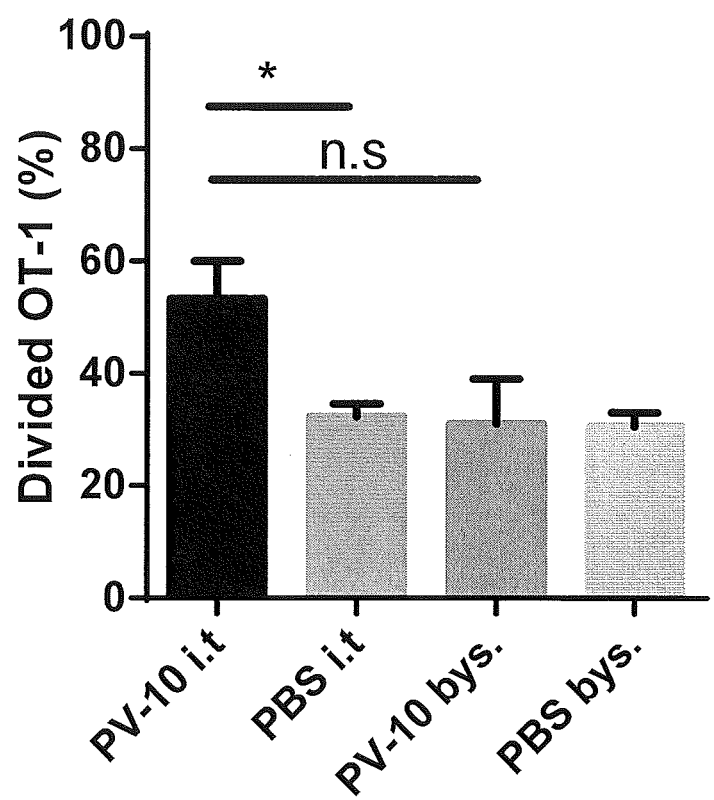

Adoptive transfer of OT-1 cells alone or treatment with IL PV-10 alone was not enough to prevent tumor progression when treatment began at day 13 with an average tumor size of 52 mm$^2$. The proliferation of OT-1 T cells in the tumor, lymph nodes (LNs) and spleen was examined after IL PV-10 injection by measurement of dye dilution of the injected CD45.1$^+$ OT-1 T-cells (FIG. 3C). OT-1 cells robustly proliferated at both the tumor site and in the proximal lymph nodes in PV-10- or PBS-treated mice on day 4 post-transfer, with more than 70% of cells having at least one additional division (compared to the cells before transfer, hereafter called "divided" T cells) (FIG. 3D).

An increased number of divided T cells were measured in spleens, tumors, and distal LNs in the mice treated with IL PV-10, compared to the mice treated with PBS (FIGS. 3C-F). There was no change found in the proximal LNs (data not shown), indicating that the OT-1 T-cell response in the draining LN may be too robust to measure a difference between treated and non-treated mice. Together, these data indicate that IL injection of PV-10 can boost tumor-specific CD8+ T-cell responses leading to prevention of tumor progression in M05-bearing mice.

IL PV-10 Leads to Dendritic Cell (DC) Activation

Because DCs are professional antigen-presenting cells capable of priming T cells, the presence of DCs in spleen and LNs was examined after IL PV-10 treatment. There was no change in the absolute number and percentage of splenic DCs on day 7 post-PV-10 injection. Consistent with previous findings, other immune subsets including CD8+ T cells and myeloid-derived suppressor cells (MDSCs) were also unchanged (data not shown), [Toomey et al., PloS one 8:e68561 (2013)].

However, the number of infiltrating DCs in the draining LNs (DLNs), but not in non-draining LNs (NDLNs), increased after 24 hours (i.e., about 1 day) of PV-10 treatment (FIG. 4A). The overall total number of cells in the DLNs was not significantly changed after treatment. After 72 hours, the number of infiltrating DCs in DLN of PV-10-treated mice decreased to the base level as in the PBS-treated mice, suggesting that the infiltration of DCs is transient.

To examine whether DCs infiltrated from the site of tumor, OVA protein labeled with FITC (FITC-OVA) was injected IL 4 hours after IL injection of PV-10 or PBS. The increased FITC+ DCs were measured in the DLNs, but not in the NDLNs (FIG. 4B) in the PV-10-treated mice, suggesting that IL PV-10 can induce DCs to uptake antigens and infiltrate into the DLNs from the tumor site.

Because enhanced OT-1 T-cell proliferation and increased DC infiltration were measured in DLNs after IL PV-10 treatment, it was hypothesized that IL injection of PV-10 leads to DC activation that is required for the tumor-specific response. To test this hypothesis, BM-derived DCs were co-cultured with supernatants from B16 tumors that were previously injected with IL PV-10 or PBS.

Figure 4C:
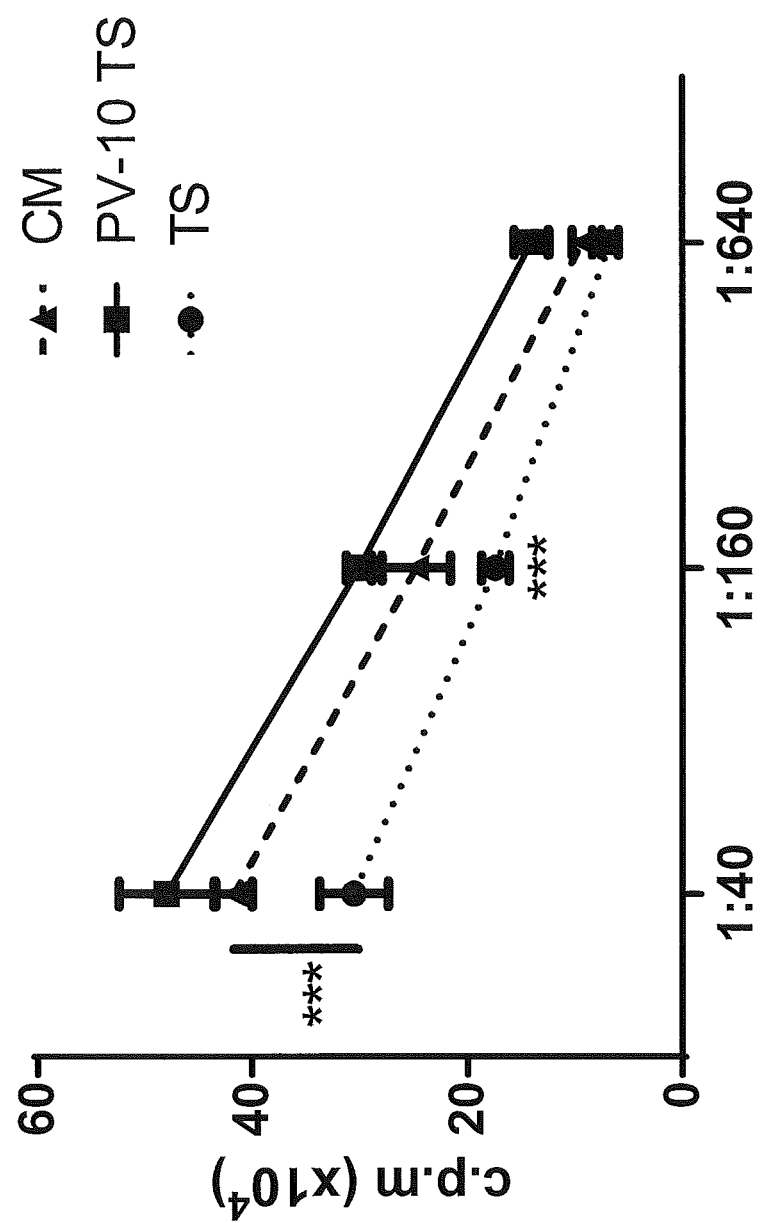
FIG. 4C is a graph showing OT-1 T-cell proliferation measured by the [3-H]-thymidine incorporation during the last 16 hours of incubation of blood mononuclear cell-derived (BM-derived) DCs that were incubated for 2 days with complete medium (CM) or tumor supernatants (TS) from B16 melanoma-bearing mice treated with IL PV-10 or PBS, then pulsed with OVA protein and co-cultured with OT-1 T-cells at different ratios for 3 days.
Figure 4D:
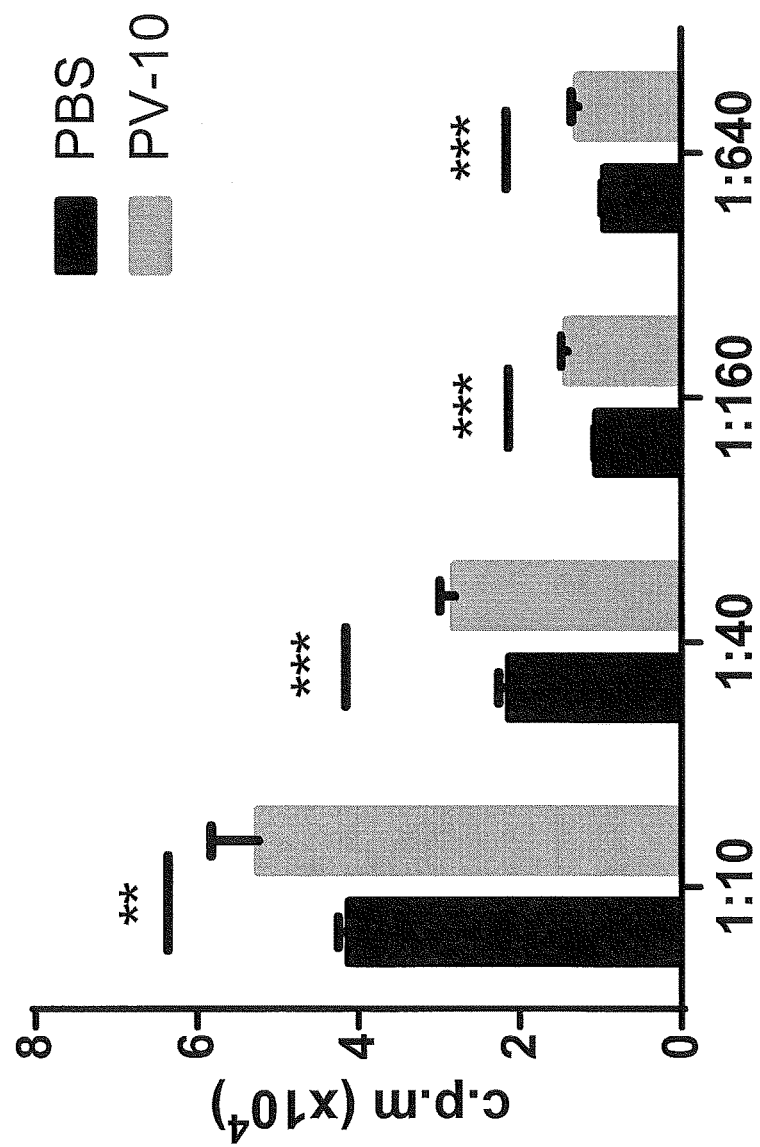
FIG. 4D is a graph comparing the numbers of BM-derived DCs that were incubated with tumor lysate from B16 cells pre-incubated with 100 µM PV-10 or PBS, pulsed with OVA protein and co-cultured with OT-1 T-cells at the stated ratios for 3 days. Cell proliferation was measured in triplicate by [3H]-thymidine uptake in the last 16 hours of culture. Data are shown as mean±SEM and are representative for two independent studies. *, p<0.05, statistically significant versus control; , p<0.01; *, p<0.001.

After being pulsed with OVA protein, DCs were co-cultured with OT-1 T-cells. DCs cultured with supernatants derived from B16 tumors from PV-10-treated mice induced increased proliferation of OT-I T-cells, compared to DC cultured with supernatants derived from B16 tumors from PBS-treated mice (FIG. 4C). In addition, DC pulsed with cell lysates of PV-10-treated cells were able to better stimulate the secretion of IFN-γ by OT-1 T-cells than DC pulsed with cell lysates of PBS-treated cells (FIG. 4D). Together, these results support the role of IL PV-10 in the activation of DCs and the increased infiltration of DCs from the tumor site into DLNs.

PV-10 Treatment Increases DC Activation Via HMGB1.

To examine how tumor death induced by IL PV-10 may be linked to the activation of DCs, PV-10-mediated cell death was investigated, as were potential factors released by tumor cells that can contribute to DC activation.

Figure 5A:
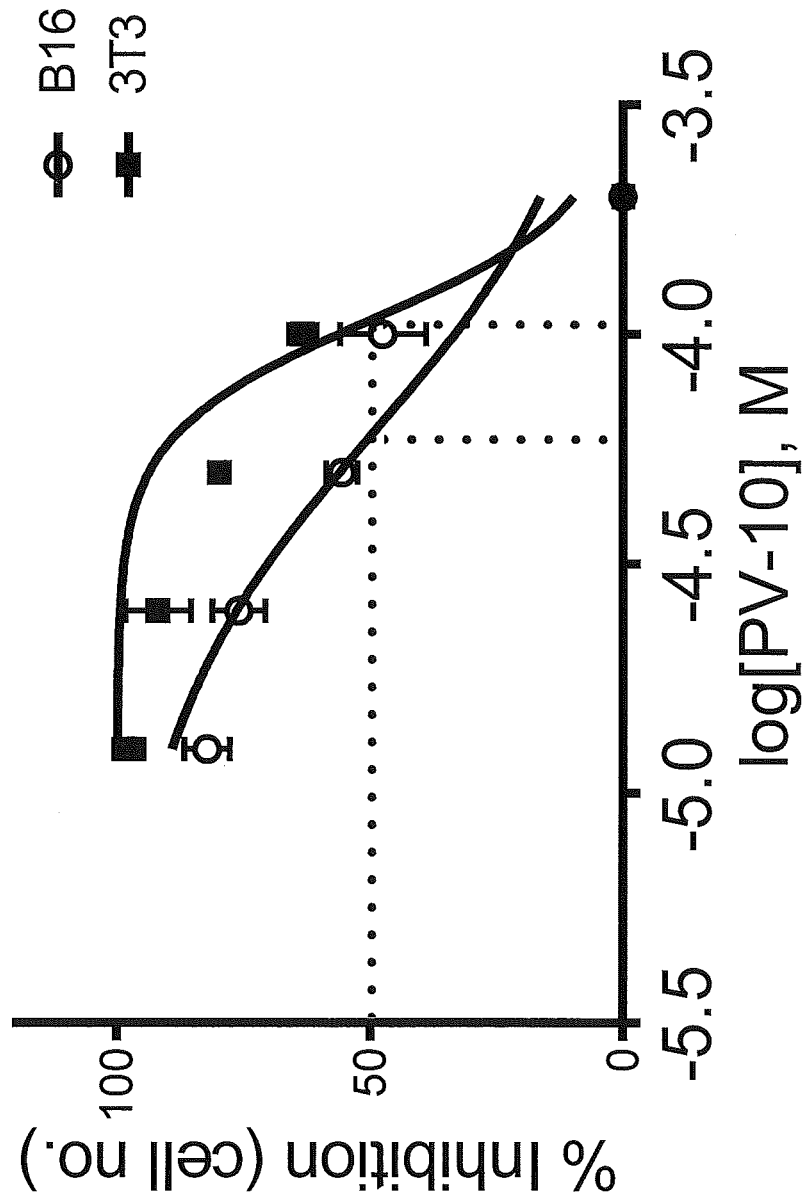
FIG. 5A is a graph showing cell death versus PV-10 concentration in mouse melanoma B16 cells, with an $IC_{50}$ of 60 µM after 48 hours, and also in the 3T3 fibroblasts, with an $IC_{50}$ of 110 µM after 48 hours.

First, the cytotoxicity of murine melanoma B16 cells mediated by PV-10 was investigated in vitro. As shown in FIG. 5A, PV-10 exhibited a dose-dependent cytotoxicity in B16 cells, with an $IC_{50}$ value of 60 μM after 48 hours of treatment. There was less cytotoxicity in mouse embryonic NIH3T3 fibroblasts, with an $IC_{50}$ value of 110 μM after 48 hours of treatment with PV-10 (FIG. 5A). The $IC_{50}$ value of PV-10 on B16 and 3T3 cells was similar at 6, 12, and 24 hours.

Figure 5B:
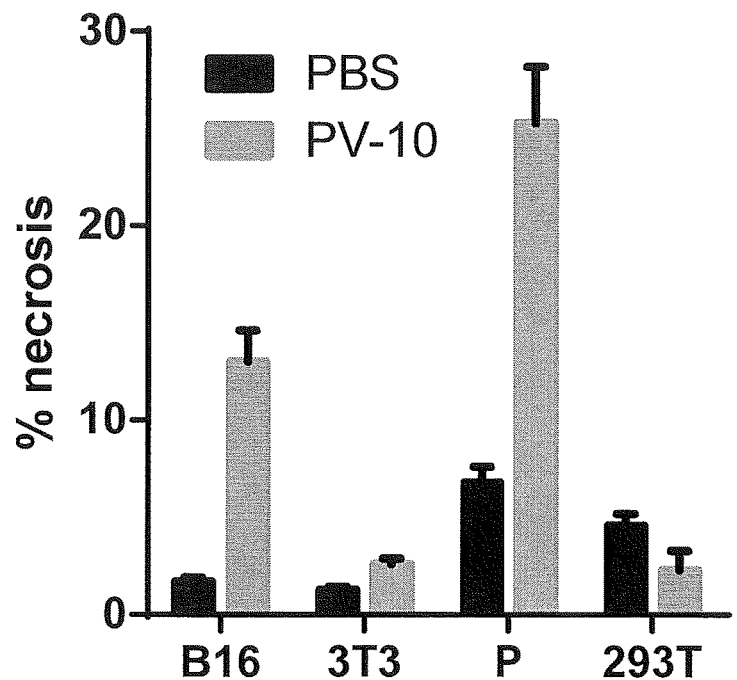
FIG. 5B is a graph that shows a flow cytometric analysis of B16 cells, 3T3 fibroblasts, human primary melanoma cells (P) and human embryonic kidney 293T cells, treated with 50 µM PV-10 for 48 hours.
Figure 5C:
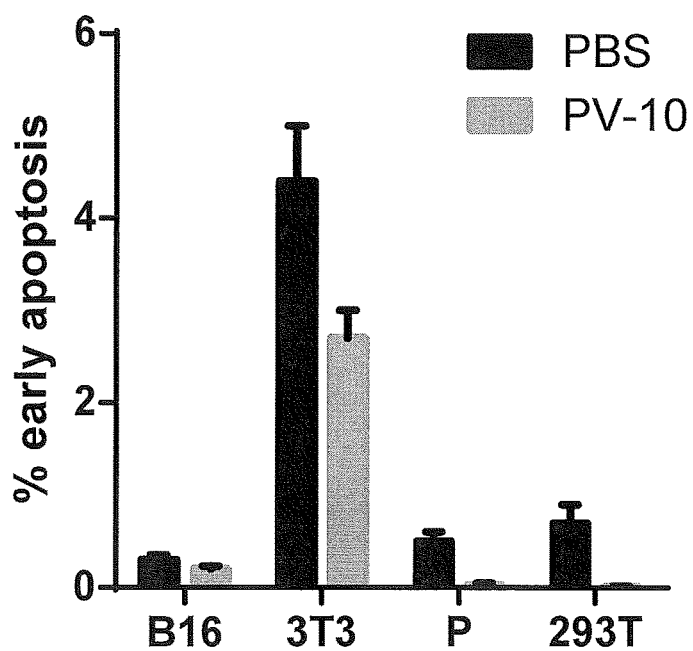
FIG. 5C is a graph that shows a flow cytometric analysis of significant increases in necrosis ($DAPI^+$) rather than early apoptosis (Annexin $V^+$ $DAPI^-$) were observed in melanoma cells treated with PV-10 as compared to PBS.

There was a significant increase in necrosis (4',6-diamidino-2-phenylindole dilactate stain; DAPI+) of B16 cells and human primary melanoma (P) cells after 48 hours of treatment with 50 μM of PV-10, whereas there was little effect on 3T3 or human embryonic kidney 293T cells (FIG. 5B). However, a relatively small proportion of cells were in early apoptosis, which is evidenced by Annexin V+™ DAPI− (BioVision, Inc., Milpitas Calif.; FIG. 5C). This also occurred 6, 12, and 24 hours after treatment. This result indicates that treatment with 50 μM of PV-10 leads to cell death through necrosis rather than apoptosis. Very few 3T3 fibroblast and human embryonic kidney 293 T cells were necrotic or apoptotic in the presence of the same dose of PV-10 (FIGS. 5B and 5C). These studies illustrate that PV-10 can kill tumor cells at a specific dose that is not toxic to non-tumor cells.

It has previously been shown that necrosis can be associated with the disruption of the integrity of the cell membrane and uncontrolled release of cytosolic contents into extracellular space. Whether tumor cells treated with PV-10 released any damage-associated molecular pattern molecules (DAMPs) was next examined.

Figure 6B:
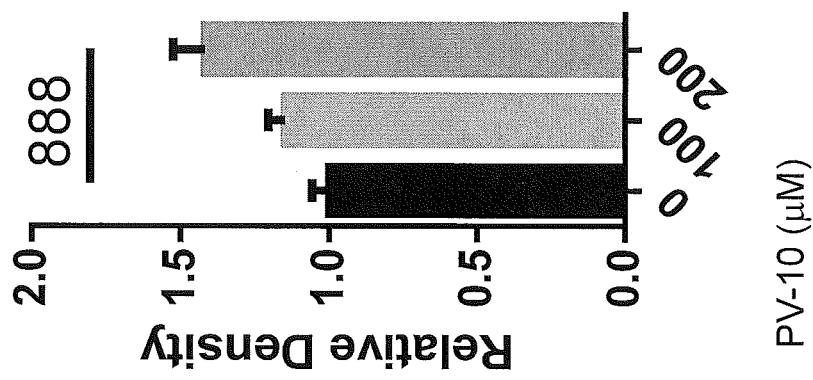
FIG. 6A and FIG. 6B are graphs of densitometric density of released HMGB1 in cell supernatants (S) as detected by western blot after treatment of B16, 3T3 cells (FIG. 6A) or human 888 melanoma cells (FIG. 6B) with noted doses of PV-10 for 48 hours. Increased HMGB1 expression was verified in cell lysates (L).
Figure 6A:
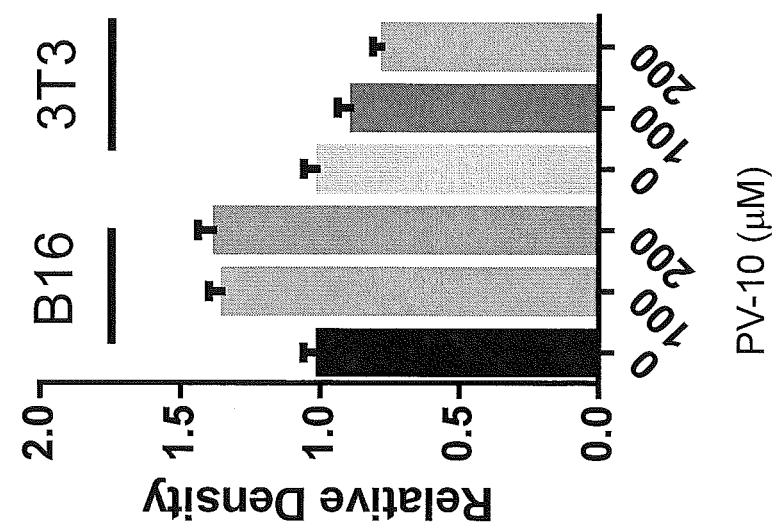

DAMPs such as HMGB1, IL-1a, and HSP proteins are known byproducts of necrosis and stimuli of DC activation. B16, 888 melanoma cells and 3T3 fibroblasts were treated with 0, 100 or 200 μM PV-10 for 48 hours. Equal amounts of supernatant were immunoblotted for HMGB1, HSP70, HSP90 or IL-1a. Treatment with PV-10 led to the release of HMGB1 into the supernatant in a dose-dependent manner from B16 cells and human melanoma 888 cells but not from 3T3 cells (FIGS. 6A and 6B). HSP 70 and IL-1α were not detected and HSP90 was unchanged after treatment with PV-10 (data not shown).

To determine if secreted HMGB1 contributed to DC activation, bone marrow- (BM-) derived DCs were incubated with 10% supernatant (TS) from B16 cells treated with PV-10 for 2 days in the presence of HMGB1 neutralizing antibody or isotype control antibody. The HMGB1 neutralizing antibody was validated by the blockade of TNF-α secretion from RAW264.7 macrophages.

Figure 6C:
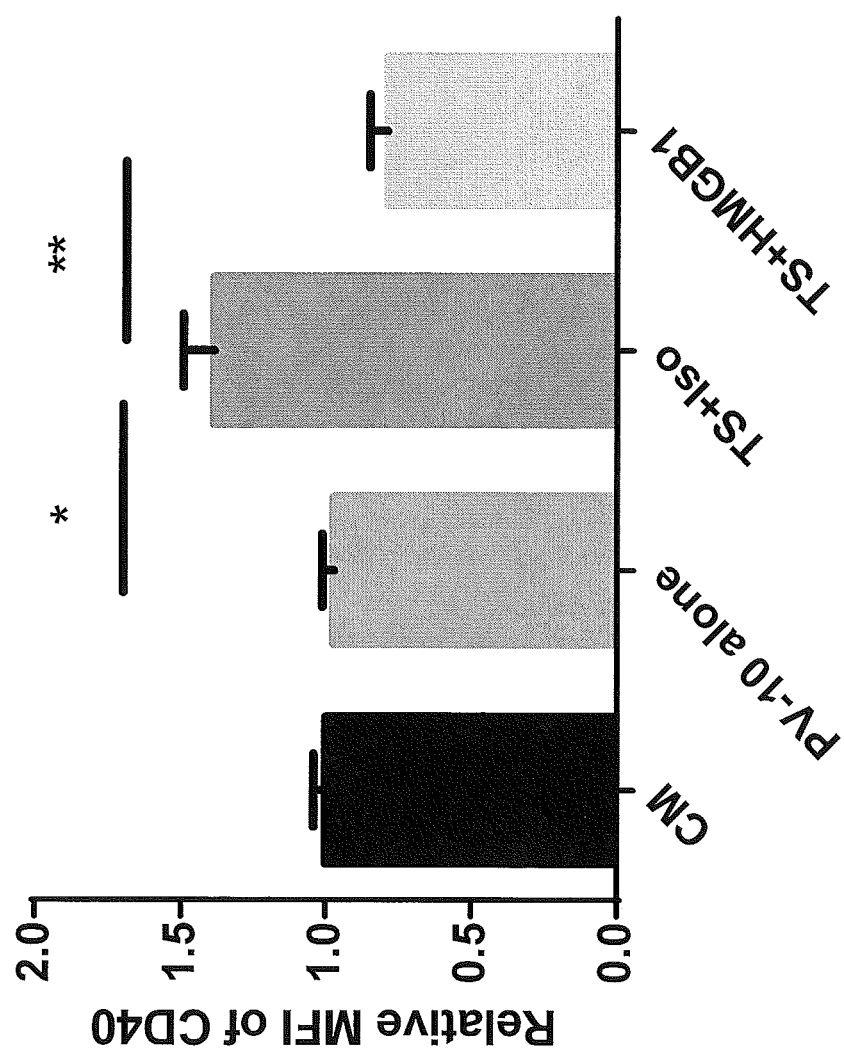
FIG. 6C is a graph of BM-derived DCs that were incubated with CM, or tumor supernatants (TS) of B16 cells that were pre-incubated with 100 µM PV-10 or PBS in the presence of HMGB1 neutralizing antibody or isotype control for 2 days. Cells were stained with antibodies against CD40 and CD11c and analyzed by flow cytometry. The relative mean fluorescence intensity (MFI) of CD40 of DCs is shown. Data are shown as mean±SEM and are representative for three independent studies. *, p<0.05, **, p<0.01

Tumor supernatant from PV-10-treated cells led to DC maturation, with up-regulation of surface CD40. Neutralization of HMGB1 significantly decreased CD40 expression (FIG. 6C). Treatment of DCs with PV-10 directly did not change CD40 expression, suggesting that PV-10 itself does not affect DC maturation. Other co-stimulatory markers on DCs, including CD86 and CD80 were not up-regulated.

Figure 6D:
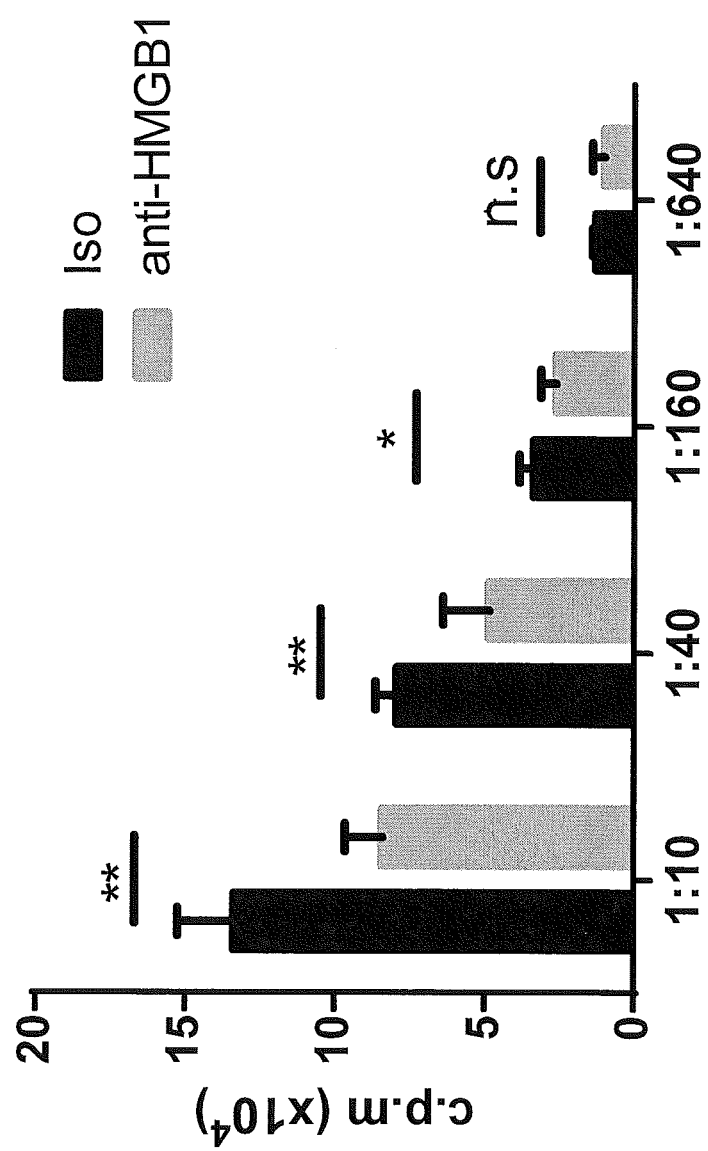
FIG. 6D is a graph of counts versus cell-to-cell culture ratios for BM-derived DCs that were incubated with tumor supernatants from M05 melanoma-bearing mice treated with IL PV-10 for 2 days, pulsed with OVA protein and co-cultured with OT-1 T-cells at stated ratios for 3 days. OT-1 T-cell proliferation was examined by the [3-H]-thymidine incorporation in the last 16 hours of culture. Data are shown as mean±SEM and are representative for two independent experiments. *, p<0.05, **, p<0.01.

To compare the antigen presentation capacity of DCs, BM-derived DC were incubated with the supernatant from M05 tumor treated with IL PV-10 in the presence of HMGB1 neutralizing antibody or isotype control antibody for 2 days. The pre-treated DCs were pulsed with OVA protein and then co-cultured with OT-1 cells to examine OT-1 T-cell proliferation. The blockade of HMGB1 reduced the ability of DCs to stimulate OT-1 T-cell proliferation (FIG. 6D), as determined by [3-H]-thymidine incorporation. This result indicates that treatment of tumor cells such as melanoma cells with PV-10 leads to the release of HMGB1, which is essential for DC activation.

To determine whether HMGB1 release was relevant to patients treated with IL PV-10, the level of HMGB1 in patients' serum before- and post-treatment with IL PV-10 was compared by measurement of IFN-γ in patient serum. The concentration of HMGB1 in patients' serum was significantly increased in samples collected 7-14 days after treatment with IL PV-10 (FIG. 7). Therefore, HMGB1 secretion appears to contribute to the bystander effect in patients with a tumor such as metastatic melanoma treated IL with PV-10.

EXAMPLES

The following examples are intended to be illustrative and non-limiting, and represent specific embodiments of the present invention.

General Methods

Human Subjects

Fourteen patients with dermal and/or subcutaneous metastatic melanoma were enrolled in a phase 1 clinical trial. (NCT01760499). Six of 14 patients had metastatic disease refractory to previous ipilimumab, anti-PD-1 and/or vemurafenib therapy, (Table 1). Two tumor lesions in each patient were sampled by biopsy pre-treatment; one of the two lesions was injected with IL PV-10, then both residual sites were completely excised 7-14 days later. Biopsy specimens were fixed in formalin and embedded in paraffin. The specimens were sectioned at 5-8 μm thickness, stained with hematoxylin and eosin stains for determination of pathologic complete response.

Immunohistochemistry was performed using CD8, CD4, CD56 and melA. Peripheral blood and serum were collected prior to, 7-14 days after IL PV-10 injection, and 21-28 days after IL PV-10 injection for analysis. Peripheral blood mononuclear cells (PBMC) were isolated by Ficoll-Paque® Plus (GE Healthcare, Pittsburgh, Pa.). Serum was prepared by collecting the supernatant after incubation of blood at room temperature for 1 hour and centrifugation at 1,000×g.

Animals

Female C57BL/6 mice (6-8 weeks old) were purchased from Harlan Laboratories (Indianapolis, Ind.). Mice were housed at the Animal Research Facility of the H. Lee Moffitt Cancer Center and Research Institute. Mice were humanely euthanized by $CO_2$ inhalation according to the American Veterinary Medical Association Guidelines. Mice were observed daily and were humanely euthanized if a solitary subcutaneous tumor exceeded 200 $mm^2$ in area or mice showed signs referable to metastatic cancer. All animal experiments were approved by the Institutional Animal Care and Use Committee and performed in accordance with the U.S. Public Health Service policy and National Research Council guidelines.

Cell Lines and Cell Culture

NIH3T3, 293T cells and melanoma B16 cells were obtained from ATCC (Manassas, Va.). Human melanoma cells 526, 624 and 888 were obtained from the NIH (Bethesda, Md.). Cells were cultured in RPMI media (cRPMI) supplemented with 10% heat-inactivated FBS, 0.1 mM nonessential amino acids, 1 mM sodium pyruvate, 2 mM fresh L-glutamine, 100 mg/ml streptomycin, 100 U/ml penicillin, 50 mg/ml gentamicin, 0.5 mg/ml fungizone (all from Life Technologies, Rockville, Md.), and 0.05 mM 2-ME (Sigma-Aldrich, St. Louis, Mo.). M05 cells expressing OVA protein [Falo et al., Nature Med 1:649-653 (1995)] were maintained in cRPMI supplemented with 0.8 mg/ml G418. The cell lines tested negative for mycoplasma contamination. All cell lines were passaged fewer than 10 times after initial revival from frozen stocks.

For in vitro study, tumor cells were incubated with a different dose of PV-10 for the indicated time. Cell supernatants were collected for functional assay or western blot. PV-10 was obtained from Provectus Biopharmaceuticals, Inc., Knoxville, Tenn.

For in vivo study, $3 \times 10^5$ tumor cells were injected into one flank of mice subcutaneously (s.c.), and on days 7 or 13 PV-10 or PBS was injected intralesionally (IL). Tumors were isolated from mice after 18 hours and digested with a tumor dissociation kit (Miltenyi Biotec, San Diego, Calif.) and GentleMACS™ (Miltenyi Biotec). Live cells were resuspended in cRPMI at a concentration of $5 \times 10^5$ cells/ml. Cell supernatants were collected for functional assays after 2 days.

FACS and Tetramer Staining

Single-cell suspensions from the indicated tissues were prepared by pressing cells through a 70 μm cell strainer. After RBC lysis with ACK buffer, cells were stained in FACS buffer with the following antibodies for flow cytometric analysis: anti-human CD3, CD4, CD8, and CD56; anti-mouse CD11c, I-$A^b$, CD45.1, CD45.2, CD86, CD80 and CD40 (all from BD Biosciences, San Diego, Calif.). For the tetramer staining, cells were stained with H-2 $K^b$/SIINFEKL tetramer (MBL international, Woburn, Mass.) at room temperature for 20 minutes, followed by an additional 20 minute incubation with additional antibodies on ice according to the manufacturer's instructions. Live/dead fixable near-IR or aqua fluorescent reactive dyes (Invitrogen™) were used to exclude dead cells before analysis. Cells were acquired by LSR II equipped with four lasers (BD Biosciences), and the data were analyzed with FlowJo® software (Tree Star, Ashland, Oreg.).

Assessment of IFN-γ and HMGB1 by ELISA For detection of IFN-γ from human samples, $CD8^+$ T-cells were isolated from PBMCs with a human $CD8^+$ T-cell isolation kit (Miltenyi Biotec). $1 \times 10^5$ cells were co-cultured with tumor cells in triplicate at a ratio of 1:1, in a U-bottom 96-well plate. After 48 hours, the IFN-γ level in the cell supernatant was measured with an IFN-γ ELISA kit (R&D Systems, Minneapolis, Minn.) according to the manufacturer's instruction.

For detection of HMGB1 in patient serum, a HMGB1 ELISA kit from IBL international (Toronto, Canada) was used according to the manufacturer's instructions.

For detection of IFN-γ in mouse samples, mice received s.c. $3 \times 10^5$ M05 cells. On day 7 after initial tumor cell injection, mice received a second injection of $3 \times 10^5$ M05 cells s.c. on the opposite flank. PV-10 or PBS (50 μL) was IL injected into the initial M05 tumor lesion on days 7 and 17. On day 23, splenocytes were collected and cultured for 7 days, in cRPMI supplemented with 1 μg/ml SIINFEKL peptide, 20 ng/ml IL-15 and 20 ng/ml IL-21 (R&D Systems) (Cheng et al., J Exp Med 205:2235-2249 (2008). The expanded cells were mixed with irradiated M05 cells at a ratio of 10:1, and IFN-γ production in the supernatants was measured after 48 hours with a IFN-γ ELISA kit (BD Biosciences) according to the manufacturer's protocol.

Adoptive Transfer of T Cells

CD45.1 OT-1 T-cells were purified with a T-cell enrichment column (R&D Systems) and were incubated with CellTracker™ Violet (Life Technologies, now Thermo Fisher Scientific, Inc. Waltham, Mass.) for 20 minutes at 37° C. After two washes in PBS, $3 \times 10^5$ labeled cells were resuspended in 100 μl of PBS and injected i.v. into M05 tumor-bearing mice. After 4 days, spleen, lymph nodes (LNs) and tumors were harvested and stained with antibodies to CD45.1 and to CD45.2. The $CD45.1^+CD45.2^-$ cells with at least one division were considered "divided cells".

DC Functional Assay

Bone marrow obtained from C57BL/6 mice was cultured with recombinant murine 20 ng/ml GM-CSF and 10 ng/ml IL-4 (R&D Systems, Minneapolis, Minn.) after RBC lysis [Liu et al., J Immunol 191:1916-1926 (2013)]. On day 5, DCs were purified with Opti-Prep™ gradient (Axis-Shield, Oslo, Norway) according to the manufacturer's protocol and cultured in the presence of GM-CSF and IL-4 at a cell density of $5 \times 10^5$ cells/ml [Vohra et al., Cancer Immunol Immun CII 59:729-736 2010)].

DCs were cultured with 10% supernatant from B16 cells incubated with 100 μM PV-10 for 2 days in the presence of an antagonistic antibody against HMGB1 (IBL international, Toronto, Canada) or the relevant isotype. Next, DCs were pulsed for 2 hours with 10 μg/ml of OVA protein (Sigma-Aldrich, St. Louis, Mo.). After multiple washes, DCs were co-cultured with $1e^5$ responder OT-1 T-cells in triplicate, in U-bottom 96-well plates at different stimulator-to-responder ratios for 3 days. $^3$H-thymidine (1 μCi) was added to each well 18 hours prior to cell harvesting. T-cell proliferation was measured by $^3$H-thymidine incorporation in a liquid scintillation counter Microbeta® Trilux (PerkinElmer, Waltham, Mass.).

Determination of $IC_{50}$

Cells were incubated with 12.5, 25, 50, 100, or 200 μM PV-10 or PBS in a 12-well plate for 6, 12, 24 and 48 hours. All wells were collected, mixed with counting beads and acquired by LSR II. DAPI was used to exclude dead cells before analysis. The absolute number of live cells was calculated by comparing the ratio of bead events to cell events. The half maximal inhibition of PV-10 on cell growth was determined as $IC_{50}$ using GraphPad Prism® software (GraphPad Software, Inc., La Jolla, Calif.).

Western Blot

For removal of cellular debris, cell supernatants were centrifuged at 14,000×g. The protein concentration of each sample was determined. Equal amounts of protein were separated on a NuPAGE® Novex® 4-12% Bis-Tris Gels (Life Technologies), then transferred onto a polyvinylidene difluoride membrane (Millipore). Membranes were blocked for 1 hour with 5% BSA (w/v) in PBS and probed with HMGB1 (cat no. 3935), HSP70 (D69), or HSP90 (C45G5) antibodies overnight at 4° C. (all from Cell Signaling Technology, Danvers, Mass.). Immunoreactivity was visualized by incubation with a horseradish peroxidase-linked secondary antibody and treatment with enhanced chemiluminescence reagents.

Statistical Analysis

The data were analyzed with a two-tailed Student's t test using GraphPad Prism® software or Wilcoxon matched pairs test. A p value of <0.05 was considered to be statistically significant.

Each of the patents, patent applications and articles cited herein is incorporated by reference. The foregoing description and the examples are intended as illustrative and are not to be taken as limiting. Still other variations within the spirit and scope of this invention are possible and will readily present themselves to those skilled in the art.

The invention claimed is:

1. A method of forming a composition of enriched tumor-specific immune anticancer agents from a host mammal comprising the steps of:
    (A) intralesionally contacting cancerous tumor tissue in a mammalian host with a tumor-ablating amount of a halogenated xanthene;
    (B) maintaining said mammalian host for a period of time sufficient to induce the mammal's immune system to produce, relative to the amount prior to treatment, a statistically significantly enhanced concentration of halogenated xanthene-induced immune anticancer components comprising one or more of a) a lymph-soluble cytokine selected from the group consisting of IL-2, TNF-α, LT, GM-CSF, IFN-γ, and HMGB1, b) immune cells that are peripheral blood mononuclear cells and c) antibodies that bind to an antigen displayed on a whole tumor cell or chemoablated cell debris;
    (C) collecting from said mammalian host a sample comprising one or more of an aliquot of peripheral blood, tumor tissue or lymphoid or lymph node tissue that contains said halogenated xanthene-induced immune anticancer components of step (B); and
    (D) culturing and preferentially expanding in vitro said halogenated xanthene-induced immune anticancer components present in said sample to form an enriched tumor-specific immune anticancer agent composition.

2. The method of claim 1, wherein said immune cells are NK cells.

3. The method of claim 1, wherein said immune cells are T cells.

4. The method of claim 1, wherein said immune cells are dendritic cells.

5. The method of claim 1, wherein said immune cells are B cells.

6. The method of claim 1, wherein said induced immune anticancer components collected in step (C) include anti-tumor antibodies and cytokines.

7. The method of claim 6, wherein said cytokines include HMGB1.

8. The method of claim 6, wherein said cytokines include IFN-γ.

9. The method of claim 1, wherein said composition of enriched tumor-specific immune anticancer agents of step (D) is further adjusted to form an immunologically-effective enriched tumor-specific immune anticancer agent preparation that contains an immunologically-effective concentration of enriched tumor-specific immune anticancer agents dissolved or dispersed in a pharmaceutically acceptable diluent, said composition also containing a parenteral injection-appropriate salt content, osmolality and pH value.

10. The method of claim 9, including the further step of collecting the immunologically-effective enriched tumor-specific immune anticancer agent preparation.

11. The method of claim 1, wherein said lymphoid tissue of step (C) includes draining lymph nodes, thymus cells and splenic cells.

12. The method of claim 1, wherein T cells are separated from said sample and are preferentially expanded in step (D).

13. The method of claim 1 including the further step of banking said sample prior to step (D).

14. The method of claim 1 including the further step of banking said sample after step (D).

15. The method of claim 1, wherein said halogenated xanthene is a compound of Formula 1 or Formula 2, below, in which $R^1$ is independently F, Cl, Br, I, H or $C_1$-$C_4$ alkyl; $R^2$, $R^3$, $R^4$, and $R^5$ are independently Cl, H or I wherein at least one substituent of $R^2$, $R^3$, $R^4$, and $R^5$ is I and at least one is Cl or H; $R^6$ independently H or $C_1$-$C_4$ alkyl; $R^{11}$ is H or $C_1$-$C_4$ alkyl; $R^{12}$ is H or $C_1$-$C_7$ acyl

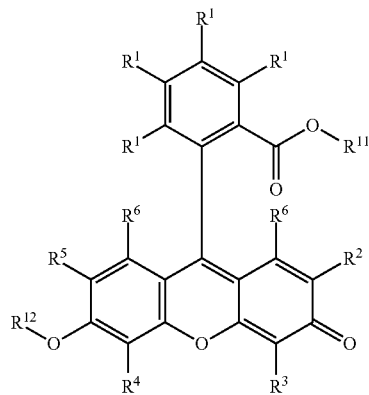

FORMULA 1

-continued

FORMULA 2

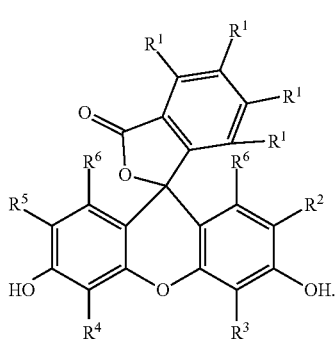

16. The method of claim 1, wherein the contacted cancerous tumor tissue is selected from one or more of the group consisting of melanoma, prostate, breast, bladder, renal, pancreatic, colon, colorectal, gall bladder, primary or metastatic liver cancer, and small cell and non-small cell lung cancer.

17. The method of claim 1, wherein the contacted cancerous tumor tissue is melanoma.

18. A method of treating an mammalian host with a cancerous tumor that comprises the step of administering an effective amount of an immunologically-effective enriched tumor-specific immune anticancer agent preparation of claim 10 to said animal host.

19. The method according to claim 18, wherein said immunologically-effective enriched tumor-specific immune anticancer agent preparation includes one or more of NK cells, T cells, B cells and dendritic cells.

20. The method according to claim 18, wherein said immunologically-effective enriched tumor-specific immune anticancer agent preparation includes one or both of HMGB1 and IFN-γ.

21. The method according to claim 18, wherein the enriched tumor-specific immune anticancer agents of said immunologically-effective enriched tumor-specific immune anticancer agent preparation are autologous to said host mammal.

22. The method according to claim 18 further including the step of administering one or more systemic inhibitors of immune system down regulation to said host mammal.

23. The method according to claim 22, wherein said systemic inhibitor of immune system down regulation is a monoclonal antibody that immunoreacts with one or more of CTLA-4, PD-1, PD-L1 and PD-L2.

24. The method according to claim 22, wherein said systemic inhibitor of immune system down regulation is administered to said host mammal after administration of said tumor-ablating amount of a halogenated xanthene and before collecting said sample that contains said induced immune anticancer components from said host mammal.

25. A method of treating an mammalian host with a plurality of cancerous tumors that comprises the steps of:
(A) contacting tissue of a first cancerous tumor in said mammalian host with a tumor-ablating amount of a halogenated xanthene;
(B) maintaining said mammalian host for a period of time sufficient to induce the mammal's immune system to produce relative to the amount prior to treatment, a statistically significant enhanced concentration of halogenated xanthene-induced immune anticancer components comprising one or more of a) a lymph-soluble cytokine selected from the group consisting of Il-2, TNF-α, LT, GM-CSF, IFN-γ, and HMGB1, b) immune cells that are peripheral blood mononuclear cells and c) antibodies that bind to an antigen displayed on a whole tumor cell or chemoablated cell debris;
(C) collecting a sample from said mammalian host comprising one or more of an aliquot of peripheral blood, tumor tissue or lymphoid or lymph node tissue that contains said halogenated xanthene-induced immune anticancer components of step (B);
(D) contacting tissue of a second cancerous tumor in said mammalian host with said induced immune anticancer components of step (C) from said mammalian host; and
(E) maintaining said mammalian host for a second period of time sufficient to induce the mammal's immune system to produce, relative to the amount prior to treatment, second induced immune anticancer components comprising one or more of a) a lymph-soluble cytokine selected from the group consisting of IL-2, TNF-α, LT, GM-CSF, IFN-γ, and HMGB1, b) immune cells that are peripheral blood mononuclear cells and c) antibodies that bind to an antigen displayed on a whole tumor cell or chemoablated cell debris.

26. The method according to claim 25 including the additional steps of:
(F) collecting a second sample comprising one or more of an aliquot of second induced immune anticancer components of step (E) from said mammalian host; and
(G) culturing and preferentially expanding in vitro said second induced immune anticancer components of step (F) present in said sample to form an enriched tumor-specific immune anticancer agent composition.

* * * * *